United States Patent
Kopelman et al.

(10) Patent No.: US 12,329,597 B2
(45) Date of Patent: Jun. 17, 2025

(54) CAPTURING TRUE BITE AND OCCLUSION CONTACTS

(71) Applicant: ALIGN TECHNOLOGY, INC., San Jose, CA (US)

(72) Inventors: Avi Kopelman, Palo Alto, CA (US); John Y. Morton, San Jose, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 517 days.

(21) Appl. No.: 17/658,495

(22) Filed: Apr. 8, 2022

(65) Prior Publication Data

US 2022/0323190 A1 Oct. 13, 2022

Related U.S. Application Data

(60) Provisional application No. 63/201,047, filed on Apr. 9, 2021.

(51) Int. Cl.

| | |
|---|---|
| *A61C 19/05* | (2006.01) |
| *A61B 6/03* | (2006.01) |
| *A61B 6/40* | (2024.01) |
| *A61B 6/51* | (2024.01) |
| *A61C 7/00* | (2006.01) |
| *A61C 9/00* | (2006.01) |
| *A61C 13/34* | (2006.01) |
| *G06T 7/11* | (2017.01) |
| *G06T 17/00* | (2006.01) |
| *G06T 19/20* | (2011.01) |

(52) U.S. Cl.
CPC .............. *A61C 19/05* (2013.01); *A61B 6/032* (2013.01); *A61B 6/4085* (2013.01); *A61B 6/51* (2024.01); *A61C 7/002* (2013.01); *A61C 9/0046* (2013.01); *A61C 9/0053* (2013.01); *A61C 13/34* (2013.01); *G06T 7/11* (2017.01); *G06T 17/00* (2013.01); *G06T 19/20* (2013.01); *G06T 2207/10081* (2013.01); *G06T 2207/30036* (2013.01); *G06T 2219/2004* (2013.01)

(58) Field of Classification Search
CPC .......... A61C 19/05; A61C 19/052; A61B 6/51
See application file for complete search history.

(56) References Cited

U.S. PATENT DOCUMENTS

| | | |
|---|---|---|
| 5,975,893 A | 11/1999 | Chishti et al. |
| 6,099,314 A | 8/2000 | Kopelman et al. |
| 6,152,731 A | 11/2000 | Jordan et al. |
| 6,309,215 B1 | 10/2001 | Phan et al. |
| 6,334,772 B1 | 1/2002 | Taub et al. |
| 6,334,853 B1 | 1/2002 | Kopelman et al. |
| 6,450,807 B1 | 9/2002 | Chishti et al. |
| 6,463,344 B1 | 10/2002 | Pavloskaia et al. |
| 6,542,249 B1 | 4/2003 | Kofman et al. |

(Continued)

*Primary Examiner* — Wen W Huang
(74) *Attorney, Agent, or Firm* — FisherBroyles, LLP

(57) ABSTRACT

A method for determining biting occlusion of a patient's teeth including generating a first 3D digital model of the patient's lower arch in non-occlusion. A second 3D digital model of the patient's upper arch in non-occlusion may be generated. A third 3D digital model of the patient's upper and lower arches in biting occlusion may be generated. The first and second 3D digital models May be aligned with corresponding teeth of the third 3D digital model to generate a fourth 3D model of the patient's teeth in biting occlusion.

18 Claims, 11 Drawing Sheets

(56) References Cited

U.S. PATENT DOCUMENTS

| | | |
|---|---|---|
| 6,633,789 B1 | 10/2003 | Nikolskiy et al. |
| 6,664,986 B1 | 12/2003 | Kopelman et al. |
| 6,697,164 B1 | 2/2004 | Babayoff et al. |
| 6,830,450 B2 | 12/2004 | Knopp et al. |
| 6,845,175 B2 | 1/2005 | Kopelman et al. |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| D925,739 S | 7/2021 | Shalev et al. |
| 11,096,765 B2 | 8/2021 | Atiya et al. |
| 11,238,586 B2 | 2/2022 | Minchenkov et al. |
| 11,367,192 B2 | 6/2022 | Kopelman et al. |
| 2007/0207441 A1 | 9/2007 | Lauren |
| 2012/0015316 A1 | 1/2012 | Sachdeva et al. |
| 2013/0317800 A1* | 11/2013 | Wu .................... G06T 19/20 703/11 |
| 2015/0142400 A1* | 5/2015 | Matov .................. G06F 30/20 345/420 |
| 2015/0235412 A1* | 8/2015 | Adamson ............. A61C 9/0053 382/154 |
| 2016/0008116 A1* | 1/2016 | Glinec .................. G06T 19/20 433/29 |
| 2016/0128624 A1* | 5/2016 | Matt .................... A61C 19/045 600/301 |
| 2019/0029784 A1 | 1/2019 | Moalem et al. |
| 2019/0060042 A1* | 2/2019 | Fisker ................. A61C 9/0046 |
| 2019/0117349 A1* | 4/2019 | Fisker .................... A61C 19/05 |
| 2019/0290408 A1* | 9/2019 | Fisker ..................... A61C 11/00 |
| 2019/0388193 A1 | 12/2019 | Saphier et al. |
| 2020/0085548 A1 | 3/2020 | Reynard et al. |
| 2020/0237289 A1* | 7/2020 | Hanssen ................. A61B 5/228 |
| 2020/0281702 A1 | 9/2020 | Kopelman et al. |
| 2020/0315434 A1 | 10/2020 | Kopelman et al. |
| 2020/0315743 A1* | 10/2020 | Raslambekov .... A61C 13/0004 |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068745 A1* | 3/2021 | Yancey .................. A61B 5/004 |
| 2021/0068773 A1 | 3/2021 | Moshe et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |
| 2023/0012297 A1* | 1/2023 | Wood ..................... G06T 17/00 |

* cited by examiner

CAPTURING TRUE BITE AND OCCLUSION CONTACTS

RELATED APPLICATIONS

This application claims the benefit under 35 U.S.C. § 119(e) of U.S. Provisional Patent Application No. 63/201,047, filed Apr. 9, 2021, which is incorporated herein, in its entirety, by this reference.

BACKGROUND

The contact between teeth of opposing arches of a patient's dentition, so called occlusal contacts, play a role in many facets of dental and orthodontic treatment. Correct occlusal contacts promote healthy teeth, appropriate chewing of food, correct jaw position, and have other benefits. Incorrect occlusal contacts may cause difficulty in chewing food, accelerated wear teeth, and other dental problems. In addition, identifying the patient's occlusal contacts may be useful in dental treatment, for example in the design of prosthetics, such as crowns.

However, current methods of identifying occlusal contacts and a patient's bite are less than ideal in a number of ways. For example, some methods involve placing a sheet of material between the patient's teeth during occlusion in order to mark the patient's occlusal contacts. Such a method necessarily interferes with the patient's true occlusal contacts because the sheet of material sits between the patient's teeth during evaluation. Other methods, such as the use of a bite plate, similarly interfere with the patient's natural bite. Digital methods, such as scanning a patient's teeth in occlusion to align the upper and lower arches fail to account for the changing positions of the patient's teeth when bite forces are applied during biting occlusion.

SUMMARY

As will be described in greater detail below, the present disclosure describes various systems and methods for determining a patient's true bite and true occlusal contacts during the application of bite forces on the teeth of the patient's arches during forced occlusal contact with each other. The bite forces cause the patient's teeth to move in response to contact between opposing teeth of the patient's jaw. Under the bite loads, the patient's teeth slidingly contact each other and cause movement of the tooth within the alveolus of the patient's jaw. The systems and methods disclosed herein may be used to measure and quantify the tooth movement during occlusion and underload. The systems and methods may use this information to plan treatment for the patient.

In addition, the systems and methods described herein may improve the functioning of a computing device and related systems by reducing computing resources and overhead for acquiring and storing updated patient data, thereby improving processing efficiency of the computing device over conventional approaches. These systems and methods may also improve the field of dental treatment, including prosthodontics and orthodontics, by analyzing data and carrying out methods that lead to more efficient use of dental resources and more accurate and beneficial dental treatments.

A method for determining biting occlusion of a patient's teeth may include generating a first 3D digital model of the patient's lower arch in non-occlusion, generating a second 3D digital model of the patient's upper arch in non-occlusion, generating a third 3D digital model of the patient's upper and lower arches in biting occlusion, and aligning teeth of the first and second 3D digital models with corresponding teeth of the third 3D digital model to generate a fourth 3D model of the patient's teeth in biting occlusion.

In some embodiments, the method may include segmenting the teeth of the first and second 3D digital models. In some embodiments, aligning the teeth of the first and second 3D digital models may include aligning the segmented teeth of the first and second 3D digital models with the corresponding teeth of the third 3D digital model.

In some embodiments, generating the first 3D digital model may include scanning the patient's lower arch, generating the second 3D digital model includes scanning the patient's upper arch, and generating the third 3D digital model includes scanning the patient's upper and lower arches in biting occlusion.

In some embodiments, the first 3D digital model may include data representing the buccal, occlusal, and lingual surfaces of the teeth of the patient's lower arch and the second 3D digital model may include data representing the buccal, occlusal, and lingual surfaces of the teeth of the patient's upper arch. In some embodiments, the third 3D digital model may include data representing the buccal surfaces of the patient's upper and lower arches.

In some embodiments, the third 3D digital model may not include data representing the lingual surfaces of at least one of the patient's upper and lower arches.

In some embodiments, generating the third 3D digital model of the patient's upper and lower arches in biting occlusion may include generating the third 3D digital model based on data generated when a biting force is applied to the patient's arches.

In some embodiments, the method may include determining distances between occlusal surfaces of a first tooth of a first of the upper and lower arches and a second tooth of a second of the upper and lower arches in occlusion with the first tooth based on the fourth 3D model.

In some embodiments, the method may include generating an occlusion map on occlusal surfaces of the first tooth based on the determined distances. In some embodiments, the method may include determining distances between occlusal surfaces of teeth of a first of the upper and lower arches and a teeth of a second of the upper and lower arches in occlusion with the teeth of the first of the arches based on the fourth 3D model. In some embodiments, the method may include generating an occlusion map on occlusal surfaces of the teeth of the first arch based on the determined distances.

In some embodiments, the method may include generating a movement vector between a position and orientation of a tooth in one of the first or second 3D digital models and a position and orientation of the tooth in the fourth 3D digital model.

In some embodiments, generating the third 3D digital model of the patient's upper and lower arches in biting occlusion may include generating a plurality of third 3D digital models of the patient's upper and lower arches in biting occlusion, each of the plurality of third digital models being generated based on data generated while the patient's arches are under a different one of a plurality of biting loads.

In some embodiments, aligning teeth of the first and second 3D digital models with corresponding teeth of the third 3D digital model to generate the fourth 3D model of the patient's teeth in biting occlusion may include aligning teeth of the first and second 3D digital models with corresponding teeth of each of the plurality of third 3D digital model to generate a plurality of fourth 3D digital models of the patient's teeth in biting occlusion.

In some embodiments, the method may include determining a trace of a contact between a first tooth of a first of the upper and lower arches and a second tooth of a second of the upper and lower arches based on contact locations between the first tooth and the second tooth in the plurality of fourth 3D digital models. In some embodiments, the method may include displaying the plurality of fourth 3D models of the teeth. In some embodiments, the method may include generating a sequence of contacts between a plurality of opposing pairs of teeth based on the plurality of fourth 3D digital models.

In some embodiments, the sequence of contacts between the plurality of opposing pairs of teeth may represent the order in which each of the plurality of opposing pairs of teeth come into contact with each other as the patient occlusally bites.

In some embodiments, the method may include scanning the patient's teeth in biting occlusion with a CBCT scanner to generate CBCT scan data, aligning the position of the patient's teeth in the fourth 3D digital model with the patient's teeth in the CBCT scan data to determine a position of a root of a tooth, and determining a location for placing an implant based on the position of the root of the tooth.

In some embodiments, the method may include generating an orthodontic retainer that accommodates the tooth movement based on the movement vector. In some embodiments, the method may include generating an occlusal surface position for a prosthetic tooth based on the occlusion map to avoid occlusal contact with a tooth that opposes the prosthetic tooth. In some embodiments, the prosthetic tooth is one of a crown, partial, or implant.

A system for determining biting occlusion of a patient's teeth may include a processor and memory having instructions that when executed by the processor, cause the system to carry out any of the methods disclosed herein.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

Figure 1:
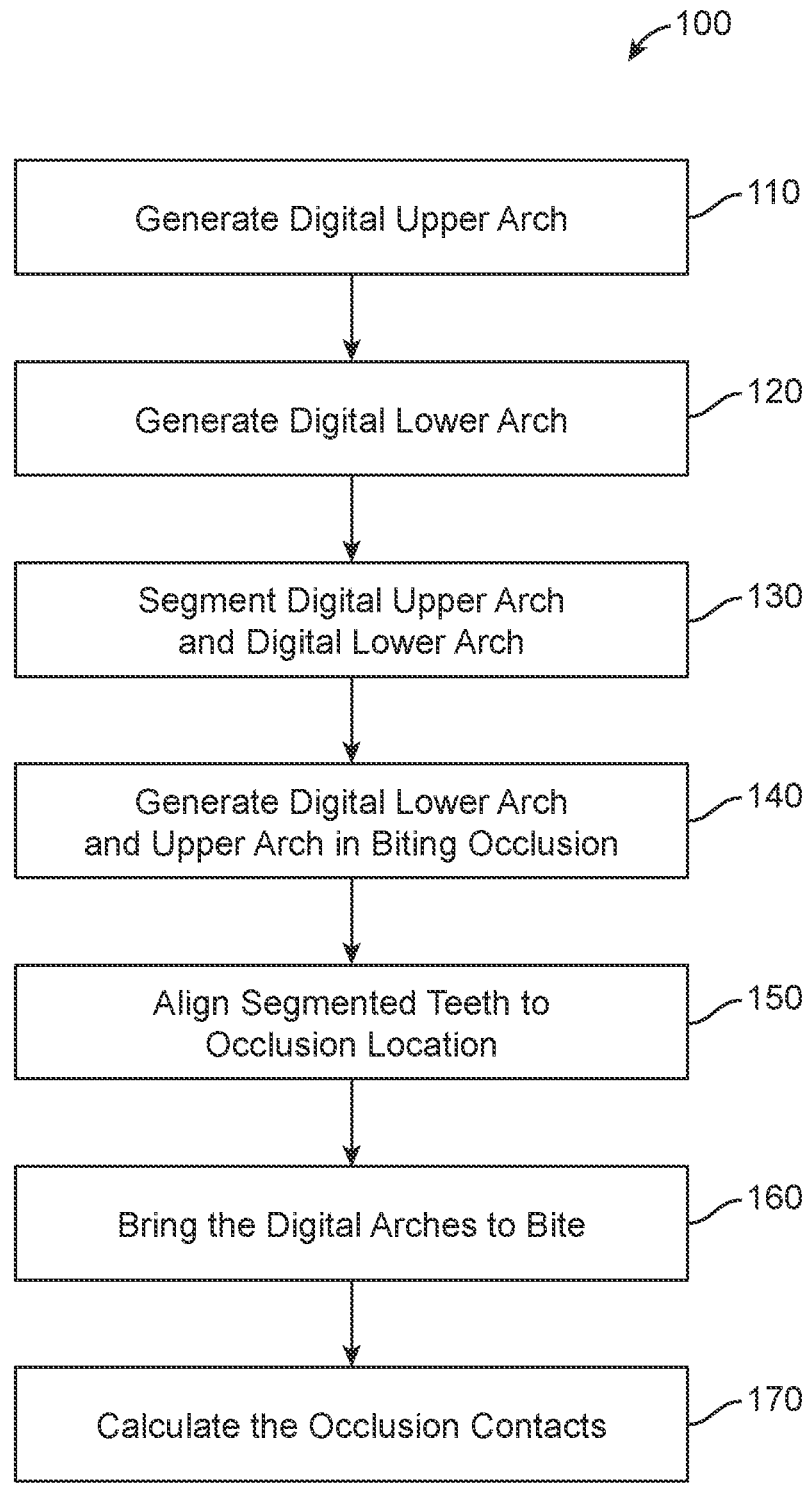
FIG. 1 shows a flow diagram of an example method of generating occlusion contacts, in accordance with some embodiments.

The FIG. 1 shows a flow diagram of an example method 100 of generating occlusion contacts. At block 110 a digital model of an upper arch is generated. A dental practitioner may use a scanning device such as a scanner to scan the external surfaces of the patient's upper arch. During the scan, the scanning device captures images and/or video of a dental site of the patient's upper arch including buccal, occlusal, and lingual surface data. In some embodiments, the scanning device captures images or video of the mesial and distal surfaces of the teeth, including the interproximal surfaces. The images and/or video may be used to generate a virtual 3D model of the upper arch. While scanning, the scanner may register and stitch together images from the intraoral scanner and generate a three-dimensional virtual model of the patient's upper arch. In some embodiments, the scan may include a full arch. In some embodiments, the scan may include less than the full arch. For example, in some embodiments, the scan may include a subset of teeth of the arch, such as a partial arch scan. In some embodiments, the scan may include teeth from partial scans of the upper arch and the lower arch. In some embodiments, the scan may include a subset of the teeth of a partial arch scan. For example, in some embodiments, opposing teeth that come into premature contact may be scanned, but at least some teeth that do not come into premature contact. In some embodiments, the teeth that come into premature contact and teeth immediately adjacent the teeth that come into premature contact may be scanned.

At block 120 a digital model of a lower arch is generated. Similar to the scanning of the upper arch, a dental practitioner may use a scanning device such as a scanner to scan the external surfaces of the patient's lower arch. During the scan, the scanning device captures images and/or video of a dental site of the patient's lower arch. The images and/or video may be used to generate a virtual 3D model of the lower arch. While scanning, the scanner may register and stitch together intraoral images from the intraoral scanner and generate a three-dimensional virtual model of the patient's lower arch. In some embodiments, the scan may include a full arch. In some embodiments, the scan may include less than the full arch. For example, in some embodiments, the scan may include a subset of teeth of the arch, such as a partial arch scan. In some embodiments, the scan may include teeth from partial scans of the upper arch and the lower arch. In some embodiments, the scan may include a subset of the teeth of a partial arch scan. For example, in some embodiments, opposing teeth that come into premature contact may be scanned, but at least some teeth that do not come into premature contact. In some embodiments, the teeth that come into premature contact and teeth immediately adjacent the teeth that come into premature contact may be scanned.

At block 130 the digital model of the upper arch and the digital model of the lower arch are segmented. During an initial scan of the patient's upper arch and lower arch, three-dimensional surface models of each individual arch are created. The digital model of the upper arch may be a single three-dimensional surface model of the upper arch and similarly, the digital model of the lower arch may be a separate single three-dimensional surface model of the lower arch. In order to carry out orthodontic and other dental assessments in treatment planning the upper and lower arch models are segmented. Segmenting an arch model separates the individual teeth and other components within the model into their own segmented or isolated model. Upon completion of the segmentation of the digital models of the upper arch and lower arch, a digital model of each tooth of the upper arch and lower arch is generated. The digital models of each tooth may be separately positionable with respect to each other.

Segmentation of the digital models may be performed in an automatic or semi-automatic manner by a processor or computing system discussed herein. The segmentation process may apply feature detection techniques to identify the characteristics of known features of the teeth in order to identify each individual tooth within the dental arch model and then extract the three-dimensional surface portions associated with the tooth to form a segmented tooth model for each tooth. Similarly, the patient's gingiva may be segmented from the initial digital model of the patient's dental arch.

After segmentation, each individual tooth of the upper and lower arch may be individually defined. The tooth definition may include a three-dimensional surface model of each individual tooth along with the tooth's position and orientation in three-dimensional space. The position and orientation of each tooth may be defined with respect to a common reference frame for each arch in both arches or the position and orientation of each tooth may be defined relative to one another. In some embodiments, the teeth of the upper arch are defined with respect to a first reference while the teeth of the lower arch are defined with respect to a second reference. In some embodiments, the first reference in the second reference are defined with respect to third, global reference.

At block 140 a digital model of the lower arch and an upper arch in biting occlusion is generated. A dental practitioner may use a scanning device such as a scanner to scan the external surfaces of the patient's upper arch and lower arch in occlusion. During the scan, the scanning device captures images and/or video of the buccal surfaces of the patient's upper arch and lower arch. In some embodiments, portions of the occlusal surfaces of the patient's teeth may also be captured. The images and/or video may be used to generate a virtual 3D model of the patient's lower arch and upper arch in occlusion. While scanning, the scanner may register and stitch together intraoral images from the intraoral scanner and generate a three-dimensional virtual model of the patient's lower arch and upper arch in occlusion. In some embodiments, the scan may include teeth from partial scans of the upper arch and the lower arch. In some embodiments, the scan may include a subset of the teeth of a partial arch scan. For example, in some embodiments, opposing teeth that come into premature contact may be scanned, but at least some teeth that do not come into premature contact are not scanned. In some embodiments, the teeth that come into premature contact and teeth immediately adjacent the teeth that come into premature contact may be scanned.

In some embodiments, purpose of the occlusal scan is to acquire sufficient information regarding the location of the patient's teeth so that the segmented tooth models generated at block 130 may be matched with the corresponding teeth and the scan generated at block 140. When scanning the patient's teeth in biting occlusion the patient is applying a biting force to their teeth rather than merely positioning their upper and lower jaws in occlusion. Accordingly, in some embodiments the dental practitioner may instruct the patient to bite down hard using a biting force. In some embodiments, the dental practitioner may instruct the patient to bite as hard as they can. By applying a biting force to the teeth in occlusion, rather than merely positioning the patient's teeth in occlusion, the patient is causing their teeth to shift or move within each tooth's alveolus.

After scanning the patient's teeth in biting occlusion, a three-dimensional surface model of the patient's teeth may be generated. In some embodiments, due to lack of access to the lingual surfaces of the teeth and most of the occlusal surfaces of the teeth, the three-dimensional surface model may not be suitable on its own for generating a full three-dimensional model of the patient's teeth in biting occlusion.

At block 150 the segmented teeth of the digital model of the upper arch and the digital model of the lower arch are aligned with the position of the patient's teeth in the digital model of the lower arch and an upper arch in biting occlusion. At block 150, the segmented models of the patient's individual teeth along with the three-dimensional surface model of the patient's upper and lower arch in occlusion may be used to generate a three-dimensional model of the patient's segmented teeth in biting occlusion.

Three-dimensional surface matching or other three-dimensional model alignment techniques may be used to match the tooth surfaces of the three-dimensional model of the patient's teeth in biting occlusion with corresponding surfaces of the individual segmented teeth generated at block 130. In some embodiments, each individual segmented tooth is placed at a location and orientation in three-dimensional space that corresponds to the location and orientation of the tooth during the scanning of the patient's teeth in biting occlusion. In this way, a segmented model of the patient's teeth of the patient's upper arch and the teeth of the patient's lower arch in biting occlusion may be formed. Such a model may be useful to dental practitioners for a variety of analysis and treatment planning purposes, some of which are discussed herein. In some embodiments, not all teeth may be scanned at block 140. If a tooth is missed or not scanned in a way that allows for alignment of the segmented teeth from block 130 with the scan of block 140, then teeth immediately adjacent to the missed tooth may be used to determine the position of the missed tooth. For example, the segmented tooth may be placed in a location between the immediately adjacent teeth such that it does not interfere with the adjacent teeth.

At block 160 the digital arches are brought into a bite position. After aligning the patient's teeth of the patient's upper arch and lower arch according to the biting occlusion scan, the digital models of the patient's upper arch and lower arch may be brought into occlusion. In some embodiments, bringing the upper arch and lower arch into biting occlusion includes moving the lower arch is moved relative to the upper arch, or vice versa, in order to orient the lower arch and the upper arch according to the scan of the patient's teeth in biting occlusion.

At block 170 the occlusion contacts are calculated. The occlusion contacts between the patient's upper arch and the patient's lower arch may be determined using the relative position of the teeth of the patient's lower arch with respect to the teeth of the patient's upper arch. An occlusal map of the occlusion contacts may be generated based on the contacts. An occlusal map may include the location and degree of contact between the teeth of the patient's upper arch and the teeth of the patient's lower arch. The occlusal map may include information such as the distance between a location on a surface of a tooth of one of the patient's upper or lower arch and a surface of a occluding tooth on the other one of the patient's upper or lower arch. In some embodiments, the distance is measured from the surface of the first tooth to the surface of the second tooth along a direction perpendicular to an occlusal plane of the patient's arch. In some embodiments, the distance is measured from the surface of the first tooth to the nearest surface of the second tooth, which may or may not be in a direction perpendicular to the occlusal plane of the patient's arch.

Figure 2:
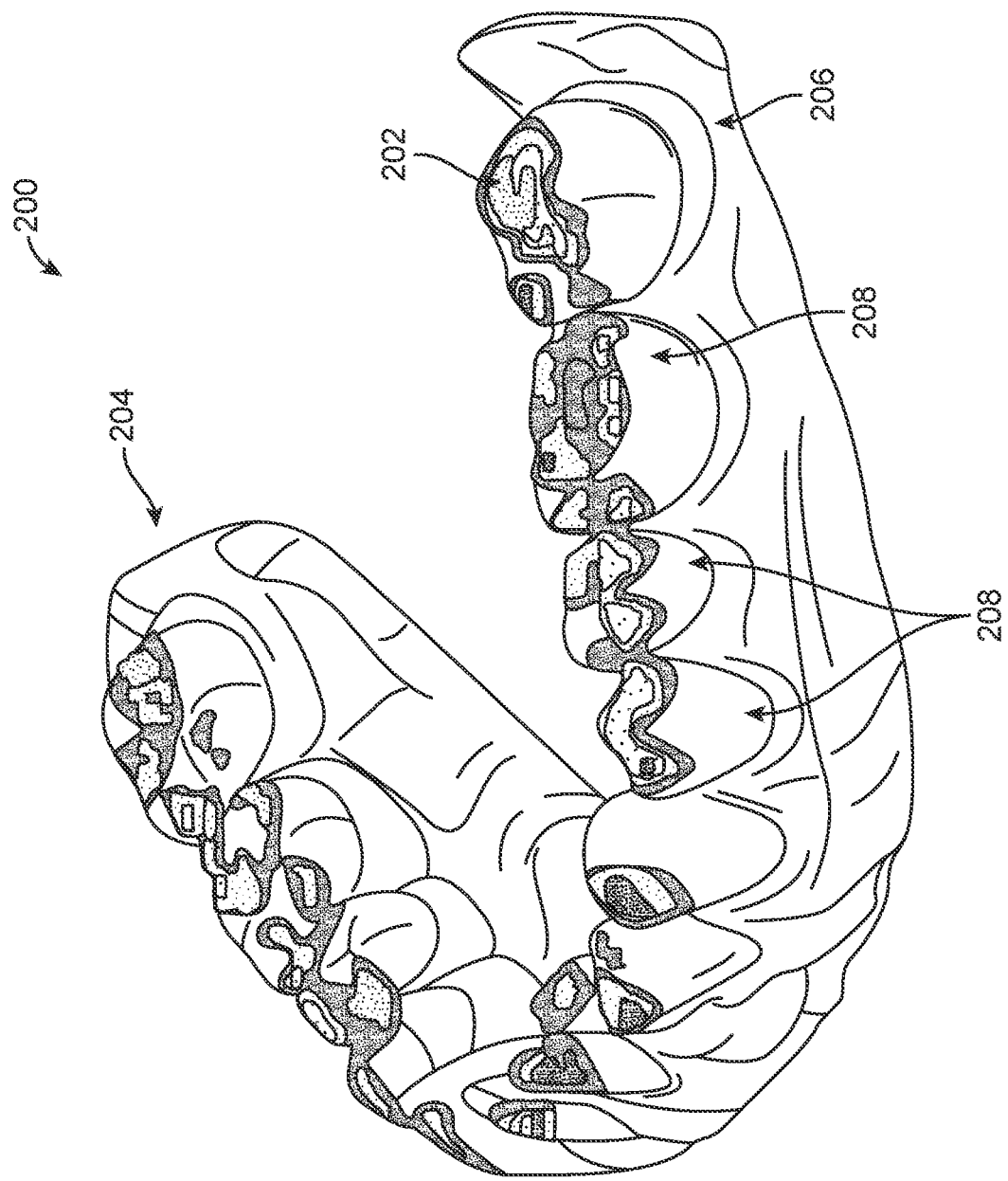
FIG. 2 shows an example of an occlusion map generated based on the occlusion contacts, in accordance with some embodiments.

FIG. 2 shows an example of an occlusion map generated based on the occlusion contacts. The occlusion map 200 depicts a three-dimensional model of the lower arch of the patient 204 including the gingiva and each of the teeth 208 of the patient's lower arch 204. The surfaces of the patient's teeth 208 are shaded to depict the degree of occlusion in occlusion map 202. The occlusion map 202 shows the relative extent of the occlusion contacts or distance between occlusal surfaces based on the shading of the respective tooth surfaces provide a digital visualization of the distance data generated at block 170. A similar occlusion map may be generated for the upper arch of the patient.

In some embodiments, a threshold may apply to the shading of the occlusion map such that if a distance is above the threshold, the distance may not be shaded. For example, occlusal distances greater than 1 mm may not be shaded while occlusal distances between zero and 1 mm may be assigned a shade or color that corresponds to an occlusal distance between zero and 1 mm. In some embodiments, occlusal distances closer to 0 mm may be assigned a red color while occlusal distances closer to 1 mm may be assigned a green color while distances in between those assigned to the red and green colors may be shaded in other colors, such as yellow and orange. Such visualizations may aid a dental practitioner in evaluating the extent of the occlusal contacts and aid in determining an appropriate dental treatment to correct any malocclusions.

Figure 3:
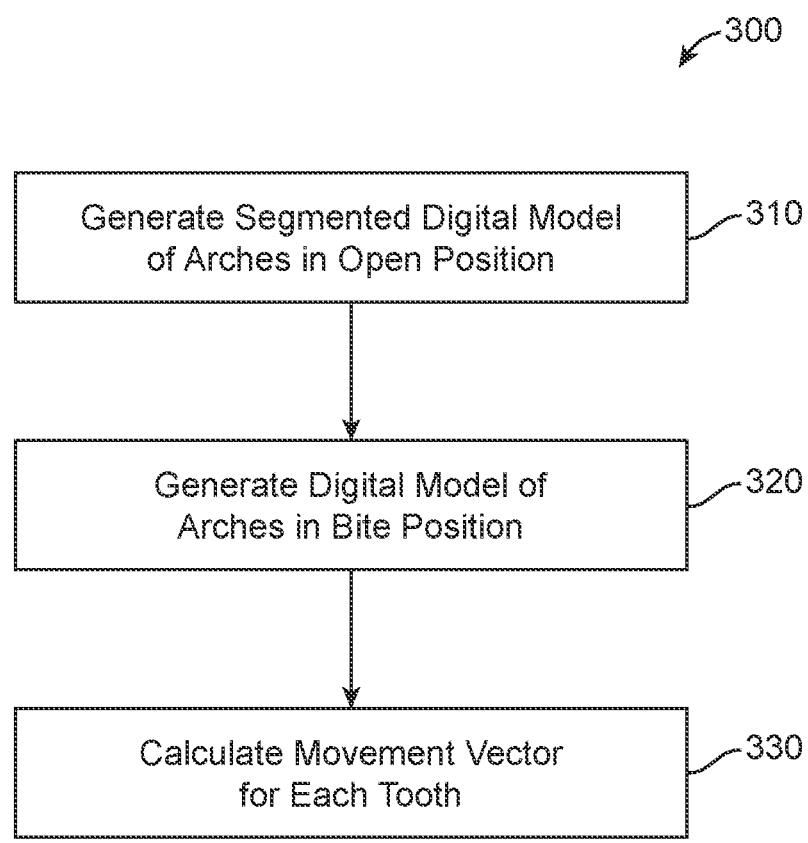
FIG. 3 shows a flow diagram of an example method for determining a tooth movement vector, in accordance with some embodiments.

FIG. 3 shows a flow diagram of an example method for determining a tooth movement vector. The tooth movement vector may be a vector between the position and orientation of a patient's tooth of an arch of the patient with respect to the arch of the patient. For example, the tooth movement vector may be a vector of an upper left canine of the patient's upper arch that represents the movement of the patient's upper left canine from an open bite position wherein the patient's arches are not in occlusion and a position of the patient's upper left canine when the patient's upper and lower arches are in biting occlusion.

At block 310 segmented digital models of the patient's arches are generated in an open position. A dental practitioner may use a scanning device such as a scanner to separately scan the external surfaces of the patient's lower arch and the external surfaces of the patient's upper arch. During each respective scan, a scanning device captures images and/or video of a dental site of the patient's respective arch. The images and/or video may be used to generate virtual 3D models of each respective arch. While scanning, the scanner may register and stitch together intraoral images from the intraoral scanner and generate a three-dimensional virtual model of each of the patient's respective arches. For example, a dental practitioner may use the scanning device to scan the patient's upper arch as discussed above with respect to block 110 and may use a scanning device to scan the patient's lower arch as discussed above with respect to block 120.

The upper arch model and the lower arch model may be segmented after scanning the patient's upper and lower arches in an open position to generate three-dimensional surface models of the patient's upper arch and lower arch. The segmentation process may be carried out in a manner as discussed above with respect to block 130. For example, segmenting the upper arch model and the lower arch model may include separating the individual teeth and other components within the models into their own segmented or isolated model. Segmentation of the digital models may be performed in an automatic or semi-automatic manner by a processor or computing system discussed herein. The segmentation process may apply feature detection techniques to identify the characteristics of known features of the teeth in order to identify each individual tooth within the dental arch model and then extract the three-dimensional surface portions associated with the tooth to form a segmented tooth model for each tooth.

After segmentation, each individual tooth of the upper and lower arch may be individually defined by a three-dimensional surface model depicting the shape of the patient's tooth along with each tooth's position and orientation.

At block 320 a digital model of the arches in a bite position is generated. In some embodiments, a dental practitioner may use a scanning device such as a scanner to scan the external surfaces of the patient's upper arch and lower arch in biting occlusion, for example, as described above with respect to block 140.

The occlusal bite scan acquires a scan of the patient's teeth in biting occlusion with sufficient information regarding the location of the patient's teeth so that the segmented tooth models generated at block 310 may be matched with the corresponding teeth in the occlusal bite scan in order to generate a vector representing the movement of the tooth or teeth between the teeth position in an open or non-occluded position and the same teeth in an occlusal bite position. When scanning the patient's teeth in biting occlusion the patient is applying a biting force to their teeth rather than merely positioning their upper and lower jaws in occlusion. In some embodiments, the dental practitioner may instruct the patient to bite down hard using a biting force. In some embodiments, the dental practitioner may instruct the patient to bite as hard as they can. By applying a biting force to the teeth in occlusion rather than merely positioning the patient's teeth in occlusion the patient is causing their teeth to shift or move within each tooth's alveolus.

After generating the occlusal bite scan, the segmented models of the patient's individual teeth along with the three-dimensional surface model of the patient's upper and lower arch in biting occlusion may be used to generate a three-dimensional model of the patient's segmented teeth in biting occlusion. The process may be carried out, for example, as discussed above with respect to block 150. In some embodiments, each individual segmented tooth is placed at a location and orientation in three-dimensional space that corresponds to the location and orientation of the tooth during the scanning of the patient's teeth in biting occlusion. In this way, a segmented model of the patient's teeth of the patient's upper arch and the teeth of the patient's lower arch in biting occlusion may be formed.

At block 330 a movement vector for each tooth is generated. The models of the patient's upper and lower arches in the open or non-occlusal position are aligned with the models of the patient's upper and lower arches in the biting occlusion. In some embodiments, for example, the digital model of the upper arch in the open or non-occlusal position is aligned in the same three-dimensional reference space as the digital model of the upper arch in the biting position. Then a movement vector between the position of each tooth in the open or non-occlusal position and the position of the tooth in the biting occlusion position is determined. The movement vector may include both a three-degree of freedom translation of the tooth, for example in X, Y, Z space, and a three-degree of freedom rotation of the tooth about the X, Y, Z axis. In this way, the movement of the tooth during biting occlusion may be determined.

Figure 4:
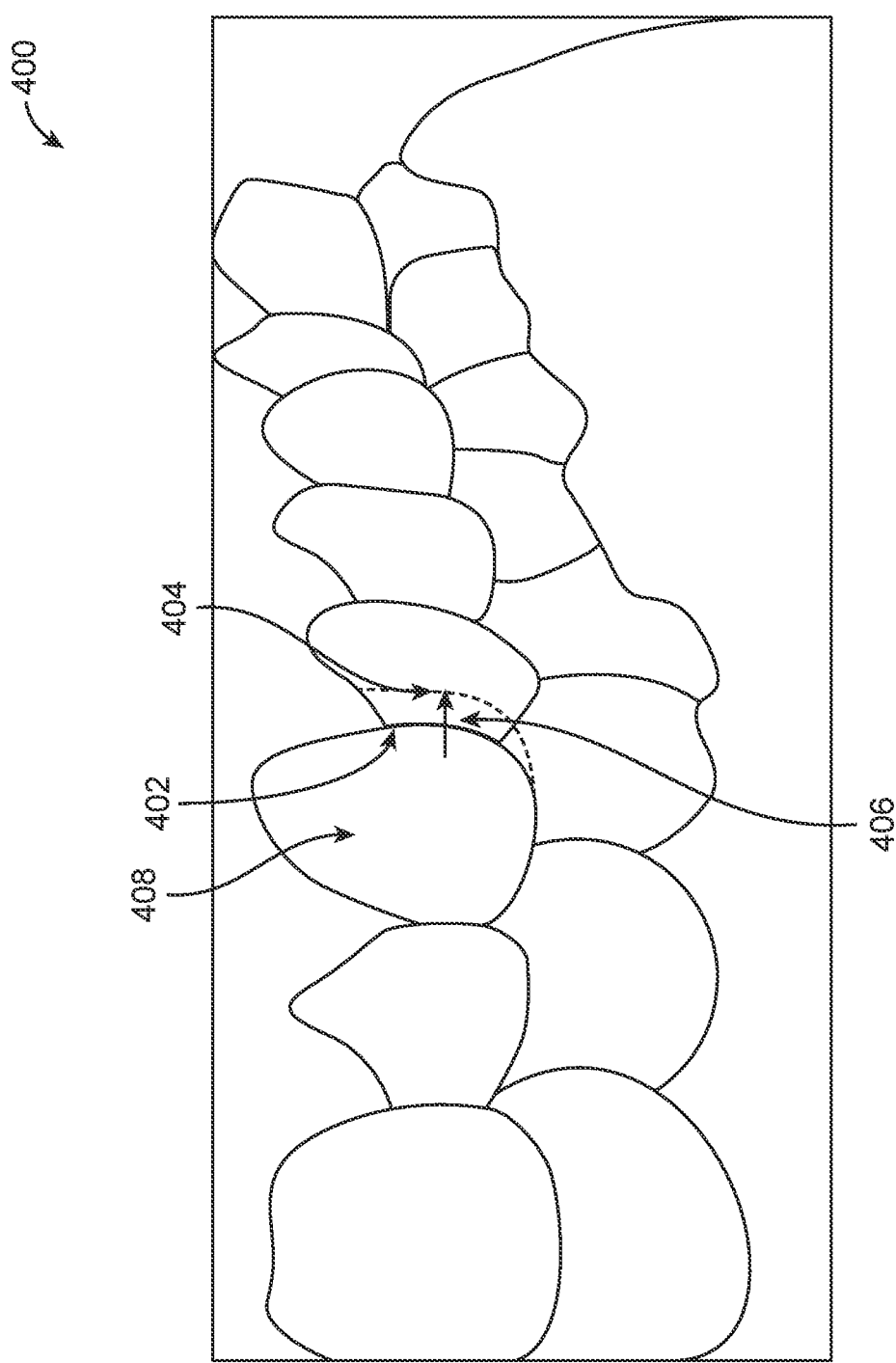
FIG. 4 shows an example tooth movement vector, in accordance with some embodiments.

FIG. 4 shows an example tooth movement vector. The digital representation 400 of the patient's teeth shows a visualization of a movement vector 406 of tooth 408. The visualization may aid dental practitioners in understanding the movement of the patient's teeth during biting occlusion. As depicted in FIG. 4, the solid outline 402 of the tooth 408 may depict the position of the patient's tooth in an open or nonoccluded state while the dashed line 404 depicts the position of the patient's teeth during biting occlusion. As shown in the digital representation 400, during biting occlusion the tooth 408 has moved as a result of the biting force applied to the patient's opposing teeth. The vector 406 shows that the tooth 408 is translated in both a distal and buccal direction without intrusion or intrusion. Although depicted from a buccal view, the movement vector and the different tooth positions may be shown from other directions, such as from a lingual view or an occlusal view.

Although both the upper arch and lower arch are depicted in the digital representation 400, in some embodiments just the upper arch or just the lower arch may be depicted in the digital representation 400. Although only a single tooth vector and the corresponding movement of tooth 408 are shown in the digital representation 400, in some embodiments multiple tooth vectors and/or corresponding tooth movement may be shown in the digital representation. For example, the movement of each tooth depicted in the digital representation 400 may be shown, with or without the corresponding movement vector. In some embodiments, tooth movement may be exaggerated in order to aid in visualizing the tooth movement. For example, tooth movement for one or both of translation and rotation may be scaled by a scaling factor in order to make the movement more apparent to the dental practitioner.

Figure 5:
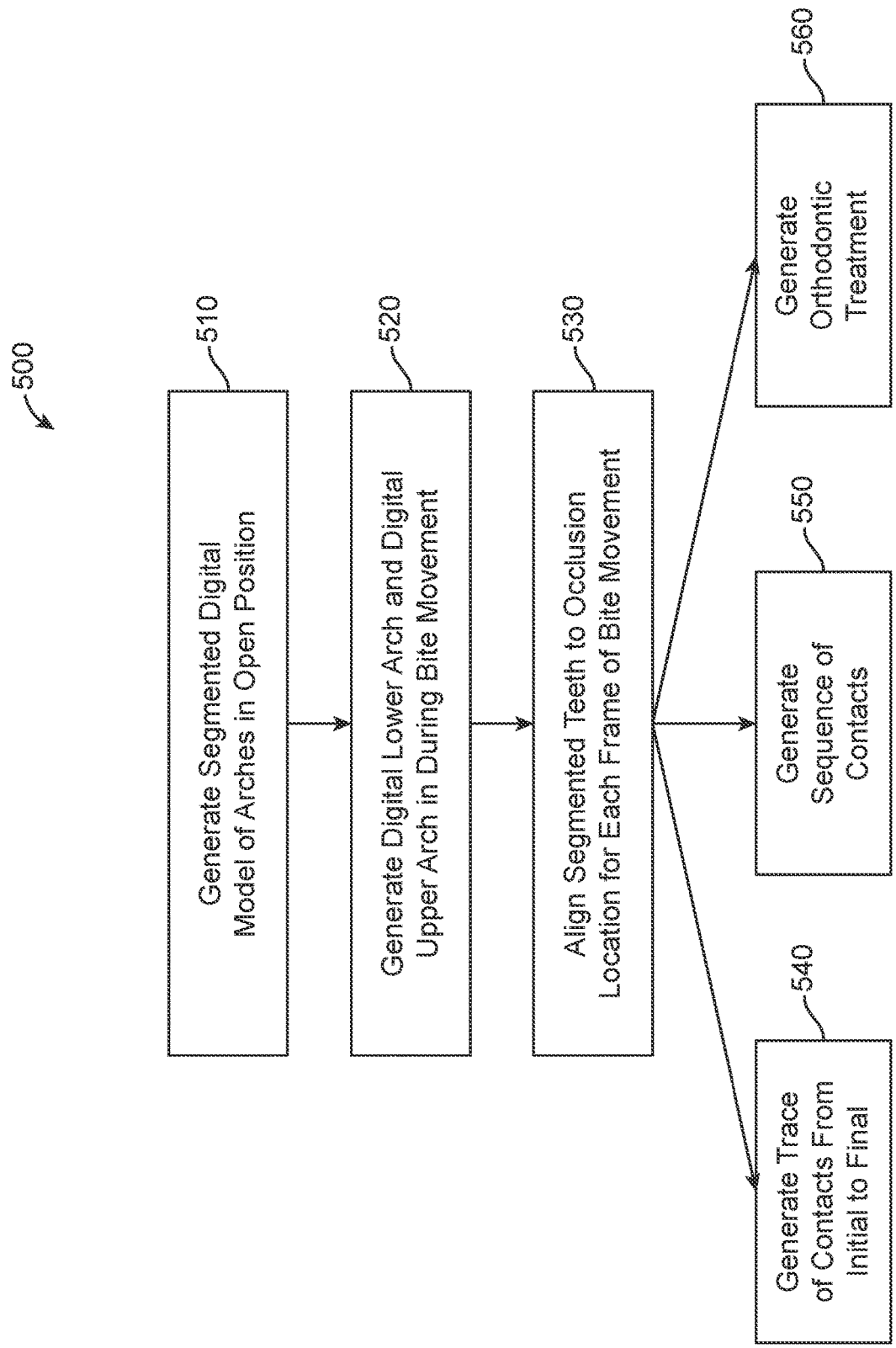
FIG. 5 shows a flow diagram of an example method for using occlusion contacts and true bite scans, in accordance with some embodiments.

FIG. 5 shows a flow diagram of an example method for using occlusion contacts and true bite scans. Occlusal contacts and movement during occlusal biting and scans of a patient's true bite during occlusal biting may be used in dental treatments such as orthodontic treatment planning, in visualizations of the patient's tooth movement, in analyzing a patient's bite, and in other dental treatments. The method 500 shows an example process for generating and using occlusal bite scans in dental treatment and analysis.

At block 510 segmented digital models of the patient's arches are generated in an open position. As discussed above, a dental practitioner may use a scanning device such as a scanner to separately scan the external surfaces of the patient's lower arch and the external surfaces of the patient's upper arch. During each respective scan, a scanning device captures images and/or video of a dental site of the patient's respective arch. The images and/or video may be used to generate virtual 3D models of each respective arch. While scanning, the scanner may register and stitch together intraoral images from the intraoral scanner and generate a three-dimensional virtual model of each of the patient's respective arches. For example, a dental practitioner may use the scanning device to scan the patient's upper arch as discussed above with respect to block 110 and may use a scanning device to scan the patient's lower arch as discussed above with respect to block 120.

The upper arch model and the lower arch model may be segmented after scanning the patient's upper and lower arches in an open position to generate a three-dimensional surface models of the patient's upper arch and lower arch. The segmentation process may be carried out in a manner as discussed above with respect to block 130. For example, segmenting the upper arch model and the lower arch model may include separating the individual teeth and other components within the models into their own segmented or isolated model. Segmentation of the digital models may be performed in an automatic or semi-automatic manner by a processor or computing system discussed herein. The segmentation process may apply feature detection techniques to identify the characteristics of known features of the teeth in order to identify each individual tooth within the dental arch model and then extract the three-dimensional surface portions associated with the tooth to form a segmented tooth model for each tooth. After segmentation, each individual tooth of the upper and lower arch may be individually defined by a three-dimensional surface model depicting the shape of the patient's tooth along with each tooth's position and orientation.

At block 520 digital models of the lower arch and the upper arch are generated during bite movement. In some embodiments, a dental practitioner may use a scanning device such as a scanner to scan the external surfaces of the patient's upper arch and lower arch and occlusion, for example, as described above with respect to Block 140.

Intraoral scanners, such as those used for scanning the patient's upper and lower arch, may generate multiple three-dimensional scans per second, for example 10 scans per second, 20 scans per second, and in some embodiments up to 600 scans per second. The multiple scans generated by such an intraoral scanner may be used to show tooth movement during the biting process. For example, in some embodiments a patient may bring their teeth into occlusion, such as light occlusion wherein the teeth of the upper and lower jaw are resting on each other and a dental practitioner may begin scanning at the this initial occlusion and continue scanning as the patient applies increasing biting forces between their upper and lower arches. In some embodiments, a patient may increase the biting force applied by the upper and lower arches from zero or an initial biting force to a final or maximum biting force over a period of time such as one second, two seconds, three seconds, or five seconds.

During the time of increasing bite force the patient's teeth may be scanned multiple times per second in order to generate a surface models of the patient's teeth as the patient applies greater and greater force between their upper and lower arches. In this way, multiple frames, each containing three-dimensional surface data of the patient's teeth, may be generated.

Intraoral scanners may have a limited field of view such that they may only view a segment of the patient's arches at any given time. In order to capture the movement of the patient's teeth during the application of biting forces the dental practitioner may scan multiple locations during multiple applications of increasing biting force by the patient. In this way, the sequence and movement of the patient's teeth during biting may be captured for the patient's entire jaw.

At block 530 the teeth of the segmented digital model of the patient's arches in the open position are aligned with each frame of the digital models of the lower arch and an upper arch generated during bite movement. The segmented models of the patient's individual teeth along with the frames representing the three-dimensional surface model of the patient's upper and lower arch as the patient applies increasing biting forces may be used to generate a three-dimensional of the patient's segmented teeth and biting occlusion for one or more frames captured during the biting process. The alignment process may be carried out for example, as discussed above with respect to block 150, for each frame. During alignment, each individual segmented tooth is placed at a location and orientation in three-dimensional space that corresponds to the location and orientation of the tooth during the scanning of the patient's teeth in biting occlusion. In this way, a segmented model of the patient's teeth of the patient's upper arch and the teeth of the patient's lower arch in biting occlusion may be formed for each frame of the biting process.

Figure 7:
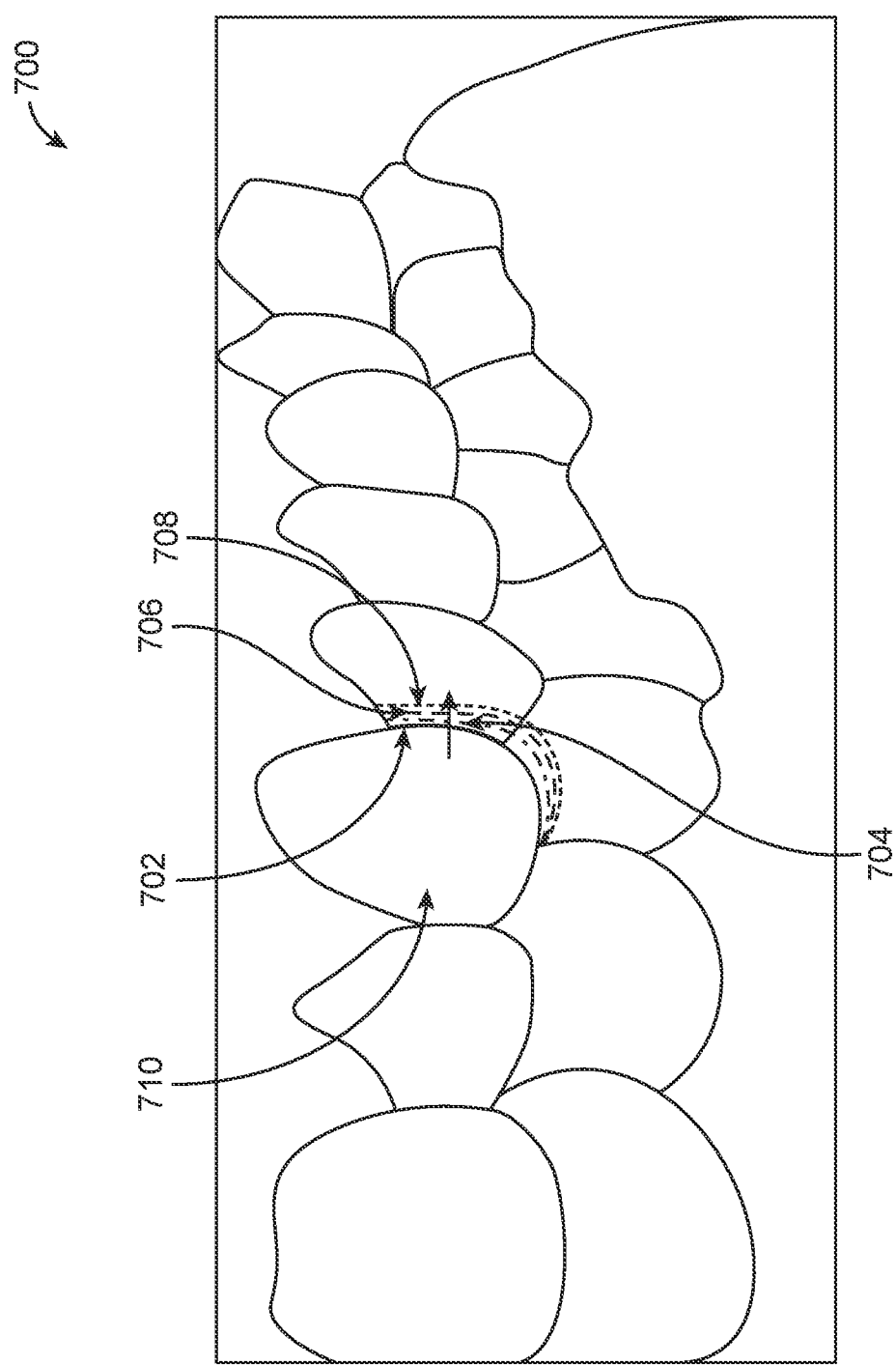
FIG. 7 shows an example tooth movement as a patient bites, in accordance with some embodiments.

With reference to FIG. 7 an example of tooth movement as a patient bites is depicted. By using the sequence of three-dimensional models generated at block 530 from the frames generated at block 520, the movement the patient's tooth as biting forces are applied may be generated. The digital representation 700 of the patient's teeth shows a visualization of a movement of the patient's tooth 710 as the patient bites. The visualization may aid in helping dental practitioners understand the movement of the patient's teeth during biting occlusion. As depicted in FIG. 7, the solid outline 702 of the tooth 710 may depict the position of the patient's tooth 710 in an open or nonoccluded state while the first dashed line 704 depicts the position of the patient's tooth during initial biting occlusion at a first biting force, while dashed line 706 and dashed line 708 depict the position of the patient's tooth during application of increasing biting force. As shown, during biting occlusion the tooth 710 has moved as a result of the force of the patient's opposing teeth imparted upon the tooth 710. Although depicted as separate dashed lines 704, 706, 708, the movement of the tooth 710 may also be depicted as sequential frames in a video which may be looped to repeatedly show the movement of the patient's tooth 710.

Although depicted from a buccal view, the movement of the tooth 710 and the different tooth positions may be shown from other directions such as from a lingual view or an occlusal view. Although both the upper arch and lower arch are depicted in the digital representation 700, in some embodiments just the upper arch or just the lower arch may be depicted in the digital representation 700. Although only the movement of a single tooth is shown in digital representation 700, in some embodiments the movement of multiple teeth may be shown in the digital representation 700. For example, the movement of each tooth depicted in the digital representation 700 may be shown. In some embodiments, the movement of the teeth may be shown with or without a corresponding movement vector, such as a movement vectors discussed above. In some embodiments, tooth movement may be exaggerated in order to aid in visualizing the tooth movement. For example, tooth movement for one or both of translation and rotation may be scaled by a scaling factor in order to make the movement more apparent to the dental practitioner.

Figure 6:
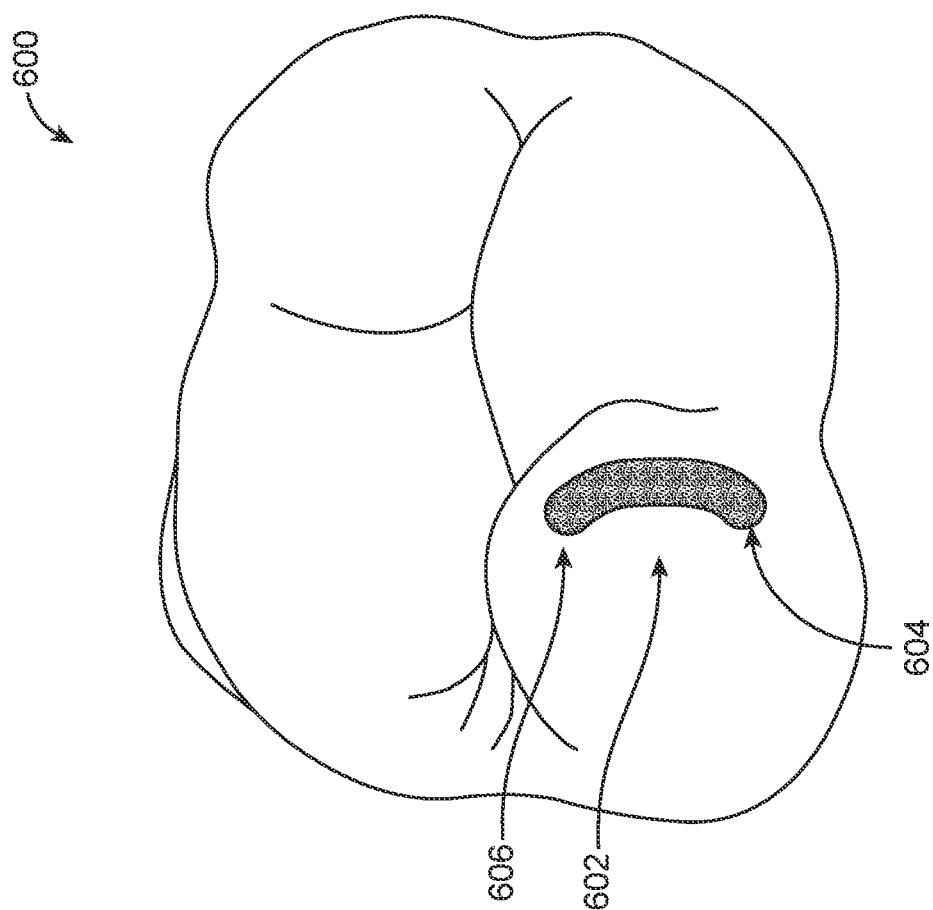
FIG. 6 shows an example contact trace, in accordance with some embodiments.

At block 540 a trace of a tooth's contact during biting is generated. An example trace of a tooth's contact during biting is shown in FIG. 6. By using the sequence of three-dimensional models generated at block 530 from the frames generated at block 520, the movement of a first tooth along the surface of another tooth during biting may be mapped. The visualization of the so-called sliding contact between opposing teeth aids in determining the movement of the patient's tooth during the bite process and in developing an appropriate treatment plan for correcting malocclusions or an improper bite of a patient.

With reference to FIG. 6, the trace 602 on the tooth 600 is shown extending along a path from a point of initial contact 604 through to the point of final contact 606. The trace 602 depicts the path of sliding contact of an opposing tooth, not shown, on the tooth 600. The point of initial contact may be a location wherein the opposing tooth initially contacts the tooth 600 as the upper and lower arch come into initial occlusion. The trace 602 shows the path of the contact as greater biting force is applied between the tooth 600 and the opposing tooth. The point of final contact may be a location where the opposing tooth contacts the tooth 600 as the patient applies the greatest biting force between their upper and lower arches. The trace 602 of the contact may also predict wear on the teeth along the trace of the contact. The trace 602 may indicate location or locations of accelerated wear on the tooth or teeth. The location of the accelerated wear may be provided to a patient to help inform them of the benefits of treatment. In some embodiments, during the treatment planning process, the final position of one or more teeth may be based on the position of the tooth at the end of sliding contact during biting.

Referring back to FIG. 5, at block 550 a sequence of contacts from a first contact the final contact is generated. The sequence of contacts may depict how the upper arch and lower arch come into contact with each other. For example, when a person brings their lower jaw into occlusion with their upper jaw, the lower jaw typically contacts the upper jaw at a first location between a first pair of opposing teeth and then at subsequent locations between subsequent pairs of opposing teeth. Generating the sequence of contacts and corresponding digital models of the patient's teeth may aid in treating a patient. The sequence of contacts may be generated based on the multiple three-dimensional models generated at block 530 from the frames generated at block 520.

At block 560 dental treatment and appliances are generated based on the true bite and occlusal contacts. In some embodiments, a dental appliance such as a retainer is generated to retain the teeth in their biting occlusion positions. In some embodiments, it may be desirable to design and fabricate a retainer that holds or maintains one or more of the patient's teeth in a biting occlusion position. In some embodiments, specific contacts between adjacent teeth in the same arch may be used to provide long term stability of the tooth positions in either or both arches. For example, one posterior tooth may be positioned behind another and in relation to the opposing teeth in order to control the bite forces and maintain the positions of the teeth. In some embodiments, analysis of the biting occlusion may show that one or more teeth have significant movement during biting occlusion, such as greater than 1 mm, greater than 2 mm, or greater than 3 mm. In such embodiments it may be desirable to design a retainer that removes all forces from these loose teeth. A retainer having a tooth receiving cavity for receiving the loose tooth may be shaped such that it does not engage, contact, or impart forces on the loose tooth during biting occlusion and/or when the patient's teeth are not in occlusion.

In some embodiments, analysis of the biting occlusion may show that one or more teeth have significant movement during biting occlusion, such as greater than 1 mm, greater than 2 mm, or greater than 3 mm. In some embodiments, a final target position of a patient's teeth may include a first posterior tooth positioned behind a second posterior tooth and in relation to the opposing teeth in order to control the bite forces and maintain the positions of the teeth at the end of treatment. The posterior teeth may be determined based on the amount of movement of the teeth during biting. In some embodiments, the first posterior tooth is the tooth with movement exceeding a threshold during biting. In some embodiments, a final target position of a patient's teeth may include positioning a cusp of a first tooth in a first arch between two cusps or withing a groove of an opposing tooth of a second arch. The opposing tooth being a tooth that occlusally contacts the first tooth. In some embodiments, the treatment planning process may include generating a target position that reduces the amount of contact sliding between teeth as compared to pre-treatment sliding, such as described with respect to FIG. 6.

In some embodiments, tooth movement in biting occlusions greater than a threshold, such as the thresholds discussed herein, may indicate a periodontally compromised tooth or teeth. In some embodiments, during the treatment planning process, one or more stages of the treatment plan may include imparting a force or forces on the teeth identified as periodontally compromised. The force may be a force through the apex of the tooth. In some embodiments, an orthodontic aligner may include a tooth receiving cavity for receiving the periodontally compromised tooth. The tooth receiving cavity may be shaped to impart a force through the apex of the tooth, such as the top of the root of the tooth. The force may be less than a threshold for moving the tooth. In some embodiments, the force may be less than 10 gram-force or less than 0.1 N. In some embodiments, the force through the apex may be less than 1 N. In some embodiments, the tooth receiving cavity for receiving a periodontally compromised tooth may be shaped to not have an undercut. In some embodiments, tooth receiving cavities of periodontally compromised posterior teeth may not have an undercut. In some embodiments, the tooth receiving cavity for receiving a periodontally compromised tooth may be shaped to not grasp the tooth during removal of the aligner.

Premature contacts in the anterior dentition may result in the upper and lower teeth shifting in the alveolus when a bite force is applied, particularly when the tooth has high mobility, such as above a threshold, such as greater than 1 mm or as otherwise discussed herein. This shift may result in the adjacent tooth contacts changing in location and is problematic when trying to create the curvature of the anterior archform. The movement of the teeth, such as through full or partial individual arch scans and in biting occlusion to generate models and data of tooth movements, may be used in treatment planning to generate a target final arch form and the tooth movement paths and tooth movement forces to move to teeth towards the target final arch form.

In some embodiments, such as with an ectopic tooth, those that are located either inside or outside of the arch, but not necessarily in complete crossbite. The shifting of these contacts, such as initial or premature contacts, may lead to apply the application of unwanted force and result in unwanted displacement of the tooth. The movement of the teeth, such as through full or partial individual arch scans and in biting occlusion to generate models and data of tooth movements, may be used in treatment planning to generate a target final arch form and the tooth movement paths and tooth movement forces to move to teeth towards the target final arch form that reduces, accounts for, is based on, or avoids the displacement caused by one or more ectopic teeth. For example, a tooth receiving cavity of an aligner may be generated to prevent the ectopic tooth from imparting movement forces on adjacent teeth. In some embodiments, the final arch position may be adjusted based on the position and movement of the ectopic tooth or teeth.

In some embodiments, a partial arch scan may be used to produce, maintain or control a space needed for the insertion of a implant. For example, a partial scan may be used to determine movement of teeth adjacent to and opposing the space for an implant and/or prosthetic.

In some embodiment, based on the tooth movement scanning in bite occlusion, during treatment planning one or more stages of a treatment plan may generate an unwanted force on the tooth which would result in an unwanted movement. The treatment plan may be altered, such as to change the movement paths in a treatment plan to during one or more stages to reduce or remove the unwanted force caused by tooth movements and tooth-to-tooth contacts.

In some embodiments, crowded upper or lower anterior teeth that alter contacts when bite force is applied may have different contact points with high friction forces at the contacts. The contact points and/or high friction caused by the tooth moments when bit force is applies may result in very little or no tooth movement occurring or less movement than planned in the treatment planning. The treatment plan may be altered, such as to change the movement paths in a treatment plan to during one or more stages to reduce or remove the unwanted contacts and allow the tooth movement to take place during treatment. In some embodiments, such as in a Class II div2 treatment in which the upper incisors are retroclined, the contacts between the upper laterals and incisors in bite occlusion, are controlled in the treatment plan for successful arch formation based on the bite occlusion tooth movements, such as by generating an orthodontic appliance configured to prevent the contacts during bite occlusion or to prevent tooth-to-tooth contact or force transfer in adjacent teeth of the same arch, such as the upper arch or the lower arch, during biting occlusion.

In some embodiments, during the treatment planning process, the final position of one or more teeth in the treatment plan may be based on the position of the tooth at the end of sliding contact during biting. In some embodiments, the final position of one or more teeth in the treatment plan may place one or more teeth at their respective locations in the bite scan. In some embodiments, the final position of one or more teeth in the treatment plan be determined based on reducing the sliding contact between teeth, such as reducing the length of the sliding contact 602 of FIG. 6 or the amount of tooth displacement during biting contact, such as shown in FIG. 7.

In some embodiments, it may be desirable to limit the allowable movement of one or more teeth based on the movement of the teeth during biting occlusion. In such embodiments, the shape of a tooth receiving cavity of the retainer or other orthodontic appliance may be shaped to allow movement along a path that corresponds to the tooth movement during biting occlusion but may restrict movement away from the path.

Determining the movement of teeth during the application of biting forces may aid in the design of orthodontic appliances for treating crossbite. In crossbite, during biting occlusion forces applied to the patient's dentition exacerbate the crossbite. The forces are also counter to the forces that are applied during orthodontic treatment in order to correct the patient's crossbite. Understanding the patient's true bite during occlusion, and designing an orthodontic appliance to counter the biting forces applied during biting occlusion may aid in more effectively treating crossbite using orthodontic aligners.

The movement of a patient's teeth during the application of biting forces may correspond to the shape of a patient's alveolus. By understanding the shape of the patient's alveolus, a treatment plan may be developed that accounts for the location of the patient's alveolus and the patient's tooth mobility therein. For example, the treatment plan may account for the relative ease of tooth's ability to move within the patient's alveolus, as compared to orthodontic movement interactions or locations outside the patient's alveolus. Stages wherein the tooth moves against the alveolus may have smaller movement steps between stages while stages wherein the tooth moves along the alveolus may have larger movement steps between stages.

In some embodiments, the patient's tooth movement and true bite may be measured at the beginning of orthodontic treatment and then again during orthodontic treatment, such as partway through the patient's orthodontic treatment. The initial and mid-treatment scans may be compared in order to evaluate changes in the patient's true bite and tooth mobility during orthodontic treatment. Changes in the patient's orthodontic treatment plan may be made based on such mid-treatment analysis.

In some embodiments, it may be desirable to stabilize the patient's jaw during or after surgery. An orthodontic appliance to stabilize the patient's jaw may be designed using the scanned true bite of the patient's teeth during biting occlusion. Such an appliance may include occlusal surfaces shaped to stabilize the patient's mandible during or after surgery.

In some embodiments, time analysis may be conducted with respect to the patient's true bite and tooth movement during biting occlusion. For example, the patient's true bite and tooth movement during biting occlusion may be measured over time, such as once a year. The patient's tooth movement, such as a vector of each tooth movement during biting occlusion, may be determined for each time. Over time, changes in the patient's tooth movement may be analyzed and treated, as appropriate.

In restorative treatment it may be desirable to limit the contacts on or between prosthetic teeth during biting occlusion. Current restorative treatments determine occlusal tooth contacts based on use the tooth position as determined in non-occlusal jaw positions. However, tooth contacts during biting occlusion may be different than tooth contacts determined based on non-occlusal tooth positions. In some embodiments, it may be desirable to have little or no contact between a prosthetic and an opposing tooth or teeth during biting occlusion. In such embodiments, the height or occlusal surface position of the prosthetic such as a crown, an implant, a partial, or other prosthetic, may be determined based on the position of the teeth in biting occlusion.

In some embodiments, the position of the patient's teeth during biting occlusion may be combined with a CBCT of the patient's dentition and jaw during biting occlusion in order to provide a more accurate model of the patient's teeth including both the crown and roots.

CBCT scans lack the fidelity of intraoral surface scans but provide subsurface images not available through intraoral surface scanning techniques. By combining the known positions of the patient's tooth crowns from an intraoral scan of the patient's teeth during biting occlusion with the CBCT scans, a three-dimensional model of the patient's teeth may be built using the tooth crown positions from the intraoral scan to more accurately determine the location of the patient's teeth in the CBCT scan. In this way, the position and orientation of the patient's teeth, including both the crown and the root, in the CBCT scan are more accurately determined. The more accurate positions of the teeth in the CBCT scan may be used in dental treatment such as in the placement of dental implants in locations that avoid or provide additional clearance from the roots of adjacent teeth in both non-biting and biting occlusion. For example, a location of a dental implant may be determined such that its position is greater than a threshold distance from the roots of the patient's teeth in both non-occlusal and in biting occlusion positions.

In some embodiments, digital 3D root models from the CBCT scan may be used with or combined with the 3D crown models from a surface scan, of the patient's teeth to generate a full tooth model with real root models. The full tooth model may be used in treatment planning, such as orthodontic treatment planning to model root to root contact and modify a treatment plan if root to root contacts are discovered during a first pass of the treatment plan.

Figure 8:
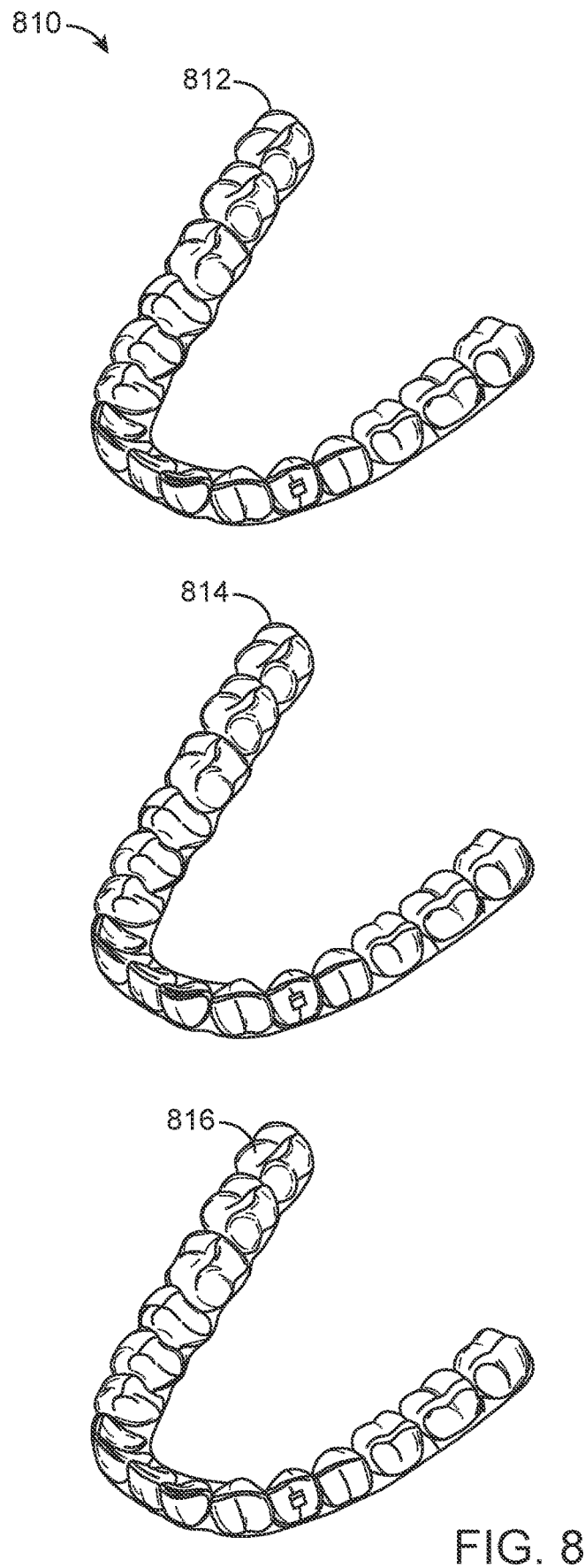
FIG. 8 shows a tooth repositioning system, in accordance with some embodiments.

FIG. 8 illustrates a tooth repositioning system 810 including a plurality of appliances 812, 814, 816. Any of the appliances described herein can be designed and/or provided as part of a set of a plurality of appliances used in a tooth repositioning system. An appliance or aligner may be worn by a patient in order to achieve an incremental repositioning of individual teeth in the jaw. The appliance can include a shell (e.g., a continuous polymeric shell or a segmented shell) having teeth-receiving cavities that receive and resiliently reposition the teeth. In one embodiment, an appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using direct fabrication techniques, from a digital model of an appliance. An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, many or most, and even all, of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements on teeth with corresponding receptacles or apertures in the appliance so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893. Examples of tooth-mounted attachments suitable for use with orthodontic appliances are also described in patents and patent applications assigned to Align Technology, Inc., including, for example, U.S. Pat. Nos. 6,309,215 and 6,830,450.

Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 810 can include a first appliance 812 corresponding to an initial tooth arrangement, one or more intermediate appliances 814 corresponding to one or more intermediate arrangements, and a final appliance 816 corresponding to a target arrangement. A target tooth arrangement can be a planned final tooth arrangement selected for the patient's teeth at the end of all planned orthodontic treatment. Alternatively, a target arrangement can be one of many intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implant, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

Figure 9:
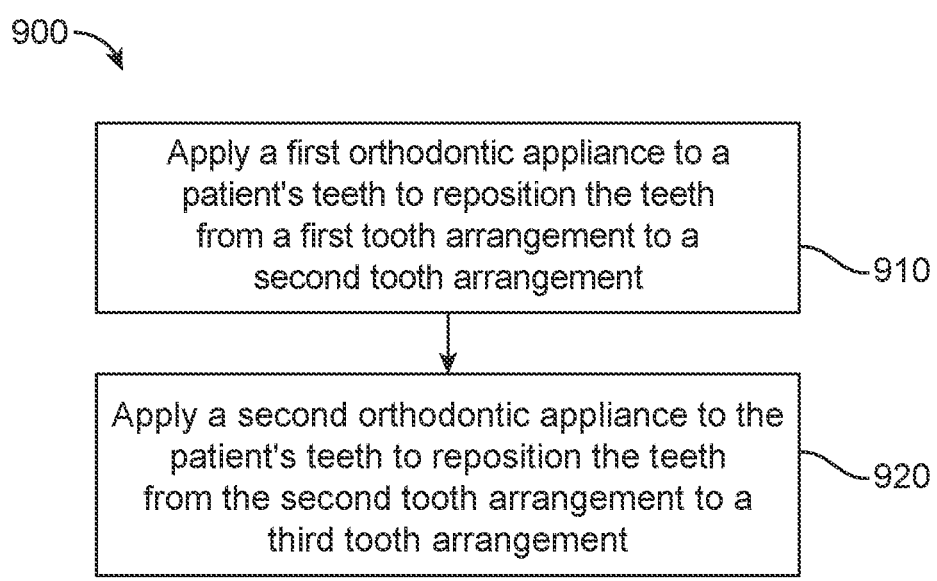
FIG. 9 shows a method of orthodontic treatment using a plurality of appliances, in accordance with embodiments.

FIG. 9 illustrates a method 900 of orthodontic treatment using a plurality of appliances, in accordance with many embodiments. The method 900 can be practiced using any of the appliances or appliance sets described herein. In step 910, a first orthodontic appliance is applied to a patient's teeth in order to reposition the teeth from a first tooth arrangement to a second tooth arrangement. In step 920, a second orthodontic appliance is applied to the patient's teeth in order to reposition the teeth from the second tooth arrangement to a third tooth arrangement. The method 900 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 10:
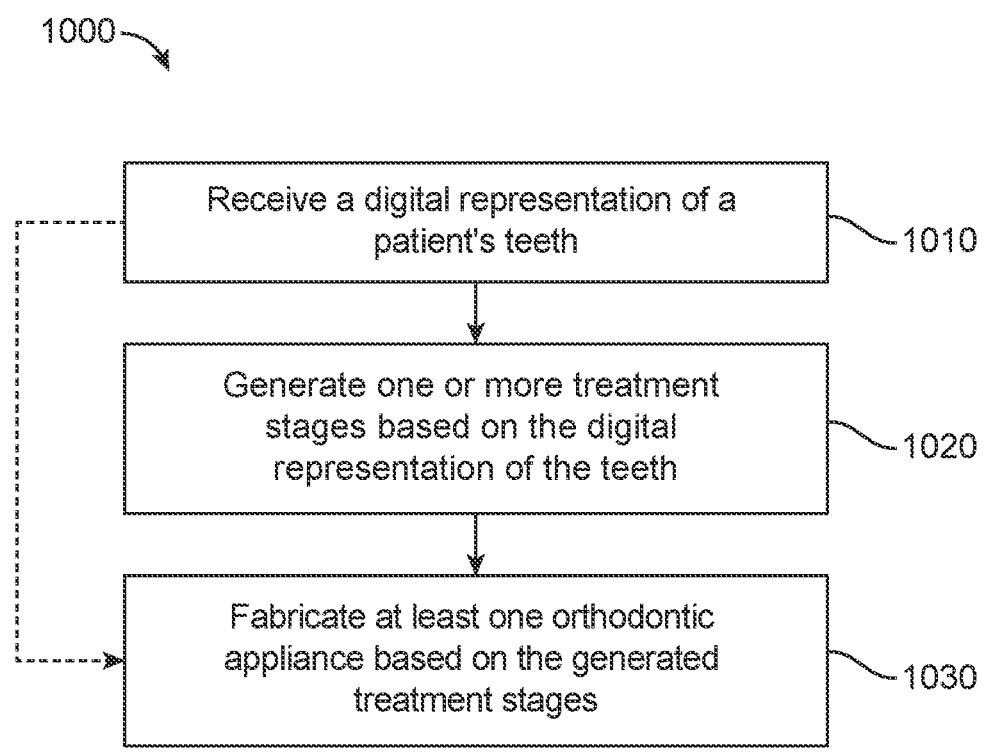
FIG. 10 shows a method for digitally planning an orthodontic treatment, in accordance with embodiments.

FIG. 10 illustrates a method 1000 for digitally planning an orthodontic treatment and/or design or fabrication of an appliance, in accordance with many embodiments. The method 1000 can be applied to any of the treatment procedures described herein and can be performed by any suitable data processing system. Any embodiment of the appliances described herein can be designed or fabricated using the method 1000.

In step 1010, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In step 1020, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In step 1030, at least one orthodontic appliance is fabricated based on the generated treatment stages. For example, a set of appliances can be fabricated to be sequentially worn by the patient to incrementally reposition the teeth from the initial arrangement to the target arrangement. Some of the appliances can be shaped to accommodate a tooth arrangement specified by one of the treatment stages. Alternatively or in combination, some of the appliances can be shaped to accommodate a tooth arrangement that is different from the target arrangement for the corresponding treatment stage. For example, as previously described herein, an appliance may have a geometry corresponding to an overcorrected tooth arrangement. Such an appliance may be used to ensure that a suitable amount of force is expressed on the teeth as they approach or attain their desired target positions for the treatment stage. As another example, an appliance can be designed in order to apply a specified force system on the teeth and may not have a geometry corresponding to any current or planned arrangement of the patient's teeth.

In some instances, staging of various arrangements or treatment stages may not be necessary for design and/or fabrication of an appliance. As illustrated by the dashed line in FIG. 10, design and/or fabrication of an orthodontic appliance, and perhaps a particular orthodontic treatment, may include use of a representation of the patient's teeth (e.g., receive a digital representation of the patient's teeth 1010), followed by design and/or fabrication of an orthodontic appliance based on a representation of the patient's teeth in the arrangement represented by the received representation.

Figure 11:
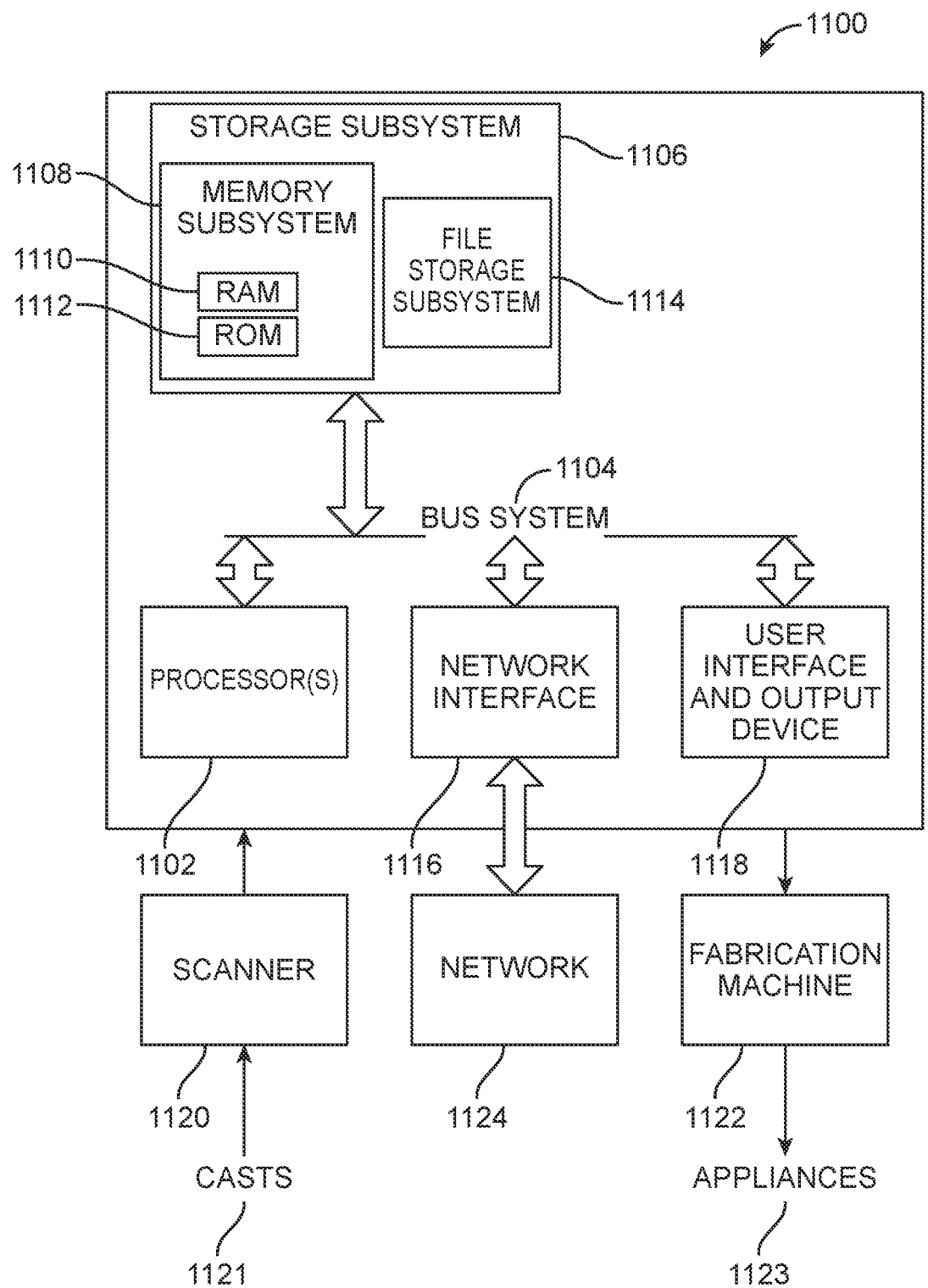
FIG. 11 shows a simplified block diagram of a data processing system, in accordance with embodiments.

FIG. 11 is a simplified block diagram of a data processing system 1400 that may be used in executing methods and processes described herein. The data processing system 1100 typically includes at least one processor 1102 that communicates with one or more peripheral devices via bus subsystem 1104. These peripheral devices typically include a storage subsystem 1106 (memory subsystem 1108 and file storage subsystem 1114), a set of user interface input and output devices 1118, and an interface to outside networks 1116. This interface is shown schematically as "Network Interface" block 1116, and is coupled to corresponding interface devices in other data processing systems via communication network interface 1124. Data processing system 1100 can include, for example, one or more computers, such as a personal computer, workstation, mainframe, laptop, and the like.

The user interface input devices 1118 are not limited to any particular device, and can typically include, for example, a keyboard, pointing device, mouse, scanner, interactive displays, touchpad, joysticks, etc. Similarly, various user interface output devices can be employed in a system of the invention, and can include, for example, one or more of a printer, display (e.g., visual, non-visual) system/subsystem, controller, projection device, audio output, and the like.

Storage subsystem 1106 maintains the basic required programming, including computer readable media having instructions (e.g., operating instructions, etc.), and data constructs. The program modules discussed herein are typically stored in storage subsystem 1106. Storage subsystem 1106 typically includes memory subsystem 1108 and file storage subsystem 1114. Memory subsystem 1108 typically includes a number of memories (e.g., RAM 1110, ROM 1112, etc.) including computer readable memory for storage of fixed instructions, instructions and data during program execution, basic input/output system, etc. File storage subsystem 1114 provides persistent (non-volatile) storage for program and data files, and can include one or more removable or fixed drives or media, hard disk, floppy disk, CD-ROM, DVD, optical drives, and the like. One or more of the storage systems, drives, etc. may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 1120 includes any means for obtaining a digital representation (e.g., images, surface topography data, etc.) of a patient's teeth (e.g., by scanning physical models of the teeth such as casts 1121, by scanning impressions taken of the teeth, or by directly scanning the intraoral cavity), which can be obtained either from the patient or from treating professional, such as an orthodontist, and includes means of providing the digital representation to data processing system 1100 for further processing. Scanner 1120 may be located at a location remote with respect to other components of the system and can communicate image data and/or information to data processing system 1100, for example, via a network interface 1124. Fabrication system 1122 fabricates appliances 1123 based on a treatment plan, including data set information received from data processing system 1100. Fabrication machine 1122 can, for example, be located at a remote location and receive data set information from data processing system 1100 via network interface 1124.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

The present disclosure includes the following numbered clauses.

Clause 1. A method for determining biting occlusion of a patient's teeth: generating a first 3D digital model of the patient's lower arch in non-occlusion; generating a second 3D digital model of the patient's upper arch in non-occlusion; generating a third 3D digital model of the patient's upper and lower arches in biting occlusion; and aligning teeth of the first and second 3D digital models with corresponding teeth of the third 3D digital model to generate a fourth 3D model of the patient's teeth in biting occlusion.

Clause 2. The method of clause 1, further comprising segmenting the teeth of the first and second 3D digital models.

Clause 3. The method of clause 2, wherein aligning the teeth of the first and second 3D digital models includes aligning the segmented teeth of the first and second 3D digital models with the corresponding teeth of the third 3D digital model.

Clause 4. The method of clause 1, wherein generating the first 3D digital model includes scanning the patient's lower arch, generating the second 3D digital model includes scanning the patient's upper arch, and generating the third 3D digital model includes scanning the patient's upper and lower arches in biting occlusion.

Clause 5. The method of clause 1, wherein the first 3D digital model includes data representing the buccal, occlusal, lingual, mesial, and distal surfaces of the teeth of the patient's lower arch and the second 3D digital model includes data representing the buccal, occlusal, lingual, mesial, and distal surfaces of the teeth of the patient's upper arch.

Clause 6. The method of clause 5, wherein the third 3D digital model includes data representing the buccal surfaces of the patient's upper and lower arches.

Clause 7. The method of clause 6, wherein the third 3D digital model does not include data representing the lingual surfaces of at least one of the patient's upper and lower arches.

Clause 8. The method of clause 1, wherein generating the third 3D digital model of the patient's upper and lower arches in biting occlusion includes generating the third 3D digital model based on data generated when a biting force is applied to the patient's arches.

Clause 9. The method of clause 1, further comprising determining distances between occlusal surfaces of a first tooth of a first of the upper and lower arches and a second tooth of a second of the upper and lower arches in occlusion with the first tooth based on the fourth 3D model.

Clause 10. The method of clause 9, further comprising generating an occlusion map on occlusal surfaces of the first tooth based on the determined distances.

Clause 11. The method of clause 1, further comprising determining distances between occlusal surfaces of teeth of a first of the upper and lower arches and a teeth of a second of the upper and lower arches in occlusion with the teeth of the first of the arches based on the fourth 3D model.

Clause 12. The method of clause 11, further comprising generating an occlusion map on occlusal surfaces of the teeth of the first arch based on the determined distances.

Clause 13. The method of clause 1, further comprising generating a movement vector between a position and orientation of a tooth in one of the first or second 3D digital models and a position and orientation of the tooth in the fourth 3D digital model.

Clause 14. The method of clause 1, wherein generating the third 3D digital model of the patient's upper and lower arches in biting occlusion includes generating a plurality of third 3D digital models of the patient's upper and lower arches in biting occlusion, each of the plurality of third digital models being generated based on data generated while the patient's arches are under a different one of a plurality of biting loads.

Clause 15. The method of clause 14, wherein aligning teeth of the first and second 3D digital models with corresponding teeth of the third 3D digital model to generate the fourth 3D model of the patient's teeth in biting occlusion includes aligning teeth of the first and second 3D digital models with corresponding teeth of each of the plurality of third 3D digital model to generate a plurality of fourth 3D digital models of the patient's teeth in biting occlusion.

Clause 16. The method of clause 15, further comprising determining a trace of a contact between a first tooth of a first of the upper and lower arches and a second tooth of a second of the upper and lower arches based on contact locations between the first tooth and the second tooth in the plurality of fourth 3D digital models.

Clause 17. The method of clause 15, further comprising displaying the plurality of fourth 3D models of the teeth.

Clause 18. The method of clause 15, further comprising generating a sequence of contacts between a plurality of opposing pairs of teeth based on the plurality of fourth 3D digital models.

Clause 19. The method of clause 15, further comprising: generating a treatment plan to move the patient's teeth from a first arrangement towards a second arrangement based on tooth positions in biting occlusion.

Clause 20. The method of clause 15, further comprising: generating a treatment plan to move the patient's teeth from a first arrangement towards a second arrangement; and modifying the tooth positions of one or more teeth during one or more stages of the treatment plan based on the tooth movements in biting occlusion.

Clause 21. The method of clause 15, further comprising: generating a treatment plan to move the patient's teeth from a first arrangement towards a second arrangement; and modifying the tooth positions of one or more teeth during one or more stages of the treatment plan based on the positions of the teeth in biting occlusion.

Clause 22. The method of clause 15, further comprising: generating a treatment plan to move the patient's teeth from a first arrangement towards a second arrangement based on tooth positions in biting occlusion, wherein the second arrangement includes positioning a first tooth relative to a second tooth to limit movement of the first or second tooth during biting occlusion to less than a threshold around.

Clause 23. The method of clause 22, wherein the threshold is 1 mm, 0.5 mm, or 0.25 mm.

Clause 24. The method of on clause 20, wherein modifying the tooth positions includes placing a cusp of a tooth of a first arch between cusps of a second tooth of a second arch in occlusion.

Clause 25. The method of on clause 20, wherein modifying the tooth positions includes placing a cusp of a tooth of a first arch within a groove of a second tooth a second arch in occlusion.

Clause 26. The method of clause 18, wherein the sequence of contacts between the plurality of opposing pairs of teeth represent the order in which each of the plurality of opposing pairs of teeth come into contact with each other as the patient occlusally bites.

Clause 27. The method of clause 1, further comprising: scanning the patient's teeth in biting occlusion with a CBCT scanner to generate CBCT scan data, aligning the position of the patient's teeth in the fourth 3D digital model with the patient's teeth in the CBCT scan data to determine a position of a root of a tooth; and determining a location for placing an implant based on the position of the root of the tooth.

Clause 28. The method of clause 13, further comprising generating an orthodontic retainer that accommodates the tooth movement based on the movement vector.

Clause 29. The method of clause 10, further comprising generating an occlusal surface position for a prosthetic tooth based on the occlusion map to avoid occlusal contact with a tooth that opposes the prosthetic tooth.

Clause 30. The method of clause 30, wherein the prosthetic tooth is one of a crown, partial, or implant.

Clause 31. The method of clause 1, wherein: generating a first 3D digital model of the patient's lower arch in non-occlusion includes generating a first 3D digital model of a portion of the patient's lower arch in non-occlusion, generating a second 3D digital model of the patient's upper arch in non-occlusion includes generating a second 3D digital model of a portion of the patient's lower arch in non-occlusion, and generating a third 3D digital model of the patient's upper and lower arches in biting occlusion includes generating a third 3D digital model of the portion of the patient's upper arch and the portion of the lower arch in biting occlusion.

Clause 32. The method of any one of clauses 1-31, further comprising generating instructions for fabricating an appliance based on the at least one of the 3D digital models.

Clause 33. The method of any one of clauses 1-31, further comprising fabricating an appliance based on the at least one of the 3D digital models.

Clause 34. The method of clause 33, wherein the appliance is an orthodontic aligner or a prosthetic tooth.

Clause 35. A system comprising: a processor; and memory having instructions that when executed by the processor, cause the system to: generate a first 3D digital model of the patient's lower arch in non-occlusion; generate a second 3D digital model of the patient's upper arch in non-occlusion; generate a third 3D digital model of the patient's upper and lower arches in biting occlusion; and align teeth of the first and second 3D digital models with corresponding teeth of the third 3D digital model to generate a fourth 3D model of the patient's teeth in biting occlusion.

Clause 36. The system of clause 35, wherein the instructions that when executed by the processor further cause the system to segment the teeth of the first and second 3D digital models.

Clause 37. The system of clause 36, wherein aligning the teeth of the first and second 3D digital models includes aligning the segmented teeth of the first and second 3D digital models with the corresponding teeth of the third 3D digital model.

Clause 38. The system of clause 35, wherein the instructions that when executed by the processor cause the system to generate the first 3D digital model further cause the system to receive scan data of the patient's lower arch, the instructions that when executed by the processor cause the system to generate the second 3D digital model further cause the system to receive scan data of the patient's upper arch, and the instructions that when executed by the processor cause the system to generate the third 3D digital model further cause the system to receive scan data of the patient's upper and lower arches in biting occlusion.

Clause 39. The system of clause 35, wherein the first 3D digital model includes data representing the buccal, occlusal, lingual, mesial, and distal surfaces of the teeth of the patient's lower arch and the second 3D digital model includes data representing the buccal, occlusal, lingual, mesial, and distal surfaces of the teeth of the patient's upper arch.

Clause 40. The system of clause 39, wherein the third 3D digital model includes data representing the buccal surfaces of the patient's upper and lower arches.

Clause 41. The system of clause 40, wherein the third 3D digital model does not include data representing the lingual surfaces of at least one of the patient's upper and lower arches.

Clause 42. The system of clause 35, wherein the instructions that when executed by the processor cause the system to generate the third 3D digital model of the patient's upper and lower arches in biting occlusion further cause the system to generate the third 3D digital model based on data generated when a biting force is applied to the patient's arches.

Clause 43. The system of clause 35, wherein the instructions that when executed by the processor cause the system further cause the system to determine distances between occlusal surfaces of a first tooth of a first of the upper and lower arches and a second tooth of a second of the upper and lower arches in occlusion with the first tooth based on the fourth 3D model.

Clause 44. The system of clause 43, wherein the instructions that when executed by the processor further cause the system to generate an occlusion map on occlusal surfaces of the first tooth based on the determined distances.

Clause 45. The system of clause 35, wherein the instructions that when executed by the processor further cause the system to determine distances between occlusal surfaces of teeth of a first of the upper and lower arches and a teeth of a second of the upper and lower arches in occlusion with the teeth of the first of the arches based on the fourth 3D model.

Clause 46. The system of clause 45, wherein the instructions that when executed by the processor further cause the system to generate an occlusion map on occlusal surfaces of the teeth of the first arch based on the determined distances.

Clause 47. The system of clause 35, wherein the instructions that when executed by the processor further cause the system to generate a movement vector between a position and orientation of a tooth in one of the first or second 3D digital models and a position and orientation of the tooth in the fourth 3D digital model.

Clause 48. The system of clause 35, wherein the instructions that when executed by the processor cause the system to generate the third 3D digital model of the patient's upper and lower arches in biting occlusion further includes instructions that cause the system to generate a plurality of third 3D digital models of the patient's upper and lower arches in biting occlusion, each of the plurality of third digital models being generated based on data generated while the patient's arches are under a different one of a plurality of biting loads.

Clause 49. The system of clause 48, wherein the instructions that when executed by the processor cause the system to generate the third 3D digital model of the patient's upper and lower arches in biting occlusion align teeth of the first and second 3D digital models with corresponding teeth of the third 3D digital model to generate the fourth 3D model of the patient's teeth in biting occlusion includes instructions to align teeth of the first and second 3D digital models with corresponding teeth of each of the plurality of third 3D digital model to generate a plurality of fourth 3D digital models of the patient's teeth in biting occlusion.

Clause 50. The system of clause 49, wherein the instructions that when executed by the processor further cause the system to determine a trace of a contact between a first tooth of a first of the upper and lower arches and a second tooth of a second of the upper and lower arches based on contact locations between the first tooth and the second tooth in the plurality of fourth 3D digital models.

Clause 51. The system of clause 49, wherein the instructions that when executed by the processor further cause the system to display the plurality of fourth 3D models of the teeth.

Clause 52. The system of clause 49, wherein the instructions that when executed by the processor further cause the system to generate a sequence of contacts between a plurality of opposing pairs of teeth based on the plurality of fourth 3D digital models.

Clause 53. The system of clause 49, wherein the instructions that when executed by the processor further cause the system to generate a treatment plan to move the patient's teeth from a first arrangement towards a second arrangement based on tooth positions in biting occlusion.

Clause 54. The system of clause 49, wherein the instructions that when executed by the processor further cause the system to: generate a treatment plan to move the patient's teeth from a first arrangement towards a second arrangement; and modify the tooth positions of one or more teeth during one or more stages of the treatment plan based on the tooth movements in biting occlusion.

Clause 55. The system of clause 49, wherein the instructions that when executed by the processor further cause the system to: generate a treatment plan to move the patient's teeth from a first arrangement towards a second arrangement; and modify the tooth positions of one or more teeth during one or more stages of the treatment plan based on the positions of the teeth in biting occlusion.

Clause 56. The system of clause 49, wherein the instructions that when executed by the processor further cause the system to: generate a treatment plan to move the patient's teeth from a first arrangement towards a second arrangement based on tooth positions in biting occlusion, wherein the second arrangement includes positioning a first tooth relative to a second tooth to limit movement of the first or second tooth during biting occlusion to less than a threshold amount.

Clause 57. The system of clause 56, wherein the threshold is 1 mm, 0.5 mm, or 0.25 mm.

Clause 58. The system of clause 54, wherein the instructions that when executed by the processor cause the system to modify the tooth positions further cause the system to place a cusp of a tooth of a first arch between cusps of a second tooth of a second arch in occlusion.

Clause 59. The system of clause 54, wherein modifying the tooth positions includes placing a cusp of a tooth of a first arch within a groove of a second tooth a second arch in occlusion.

Clause 60. The system of clause 52, wherein the sequence of contacts between the plurality of opposing pairs of teeth represent the order in which each of the plurality of opposing pairs of teeth come into contact with each other as the patient occlusally bites.

Clause 61. The system of clause 35, wherein the instructions that when executed by the processor further cause the system to: scan the patient's teeth in biting occlusion with a CBCT scanner to generate CBCT scan data, align the position of the patient's teeth in the fourth 3D digital model with the patient's teeth in the CBCT scan data to determine a position of a root of a tooth; and determine a location for placing an implant based on the position of the root of the tooth.

Clause 62. The system of clause 47, wherein the instructions that when executed by the processor further cause the system to generate an orthodontic retainer that accommodates the tooth movement based on the movement vector.

Clause 63. The system of clause 44, wherein the instructions that when executed by the processor further cause the system to generate an occlusal surface position for a prosthetic tooth based on the occlusion map to avoid occlusal contact with a tooth that opposes the prosthetic tooth.

Clause 64. The system of clause 63, wherein the prosthetic tooth is one of a crown, partial, or implant.

Clause 65. The system of clause 35, wherein the instructions that when executed by the processor cause the system to generate a first 3D digital model of the patient's lower arch in non-occlusion further causes the system to generate a first 3D digital model of a portion of the patient's lower arch in non-occlusion, the instructions that when executed by the processor cause the system to generate a second 3D digital model of the patient's upper arch in non-occlusion further causes the system to generate a second 3D digital model of a portion of the patient's lower arch in non-occlusion, and the instructions that when executed by the processor cause the system to generate a third 3D digital model of the patient's upper and lower arches in biting occlusion further causes the system to generate a third 3D digital model of the portion of the patient's upper arch and the portion of the lower arch in biting occlusion.

Clause 66. The system of any one of clauses 35-65, wherein the instructions that when executed by the processor further cause the system generate instructions for fabricating an appliance based on the at least one of the 3D digital models.

Clause 67. The system of any one of clauses 35-65, wherein the instructions that when executed by the processor further cause the system fabricate an appliance based on the at least one of the 3D digital models.

Clause 68. The system of clause 67, wherein the appliance is an orthodontic aligner or a prosthetic tooth.

Clause 69. A non-transitory computer readable medium, having stored thereon, instructions that when executed by a computing device, cause the computing device to: generate a first 3D digital model of the patient's lower arch in non-occlusion; generate a second 3D digital model of the patient's upper arch in non-occlusion; generate a third 3D digital model of the patient's upper and lower arches in biting occlusion; and align teeth of the first and second 3D digital models with corresponding teeth of the third 3D digital model to generate a fourth 3D model of the patient's teeth in biting occlusion.

Clause 70. The non-transitory computer readable medium of clause 69, wherein the instructions that when executed by the processor further cause the system to segment the teeth of the first and second 3D digital models.

Clause 71. The non-transitory computer readable medium of clause 70, wherein aligning the teeth of the first and second 3D digital models includes aligning the segmented teeth of the first and second 3D digital models with the corresponding teeth of the third 3D digital model.

Clause 72. The non-transitory computer readable medium of clause 69, wherein the instructions that when executed by the processor cause the system to generate the first 3D digital model further cause the system to receive scan data of the patient's lower arch, the instructions that when executed by the processor cause the system to generate the second 3D digital model further cause the system to receive scan data of the patient's upper arch, and the instructions that when executed by the processor cause the system to generate the third 3D digital model further cause the system to receive scan data of the patient's upper and lower arches in biting occlusion.

Clause 73. The non-transitory computer readable medium of clause 69, wherein the first 3D digital model includes data representing the buccal, occlusal, lingual, mesial, and distal surfaces of the teeth of the patient's lower arch and the second 3D digital model includes data representing the buccal, occlusal, lingual, mesial, and distal surfaces of the teeth of the patient's upper arch.

Clause 74. The non-transitory computer readable medium of clause 73, wherein the third 3D digital model includes data representing the buccal surfaces of the patient's upper and lower arches.

Clause 75. The non-transitory computer readable medium of clause 74, wherein the third 3D digital model does not include data representing the lingual surfaces of at least one of the patient's upper and lower arches.

Clause 76. The non-transitory computer readable medium of clause 69, wherein the instructions that when executed by the processor cause the system to generate the third 3D digital model of the patient's upper and lower arches in biting occlusion further cause the system to generate the third 3D digital model based on data generated when a biting force is applied to the patient's arches.

Clause 77. The non-transitory computer readable medium of clause 69, wherein the instructions that when executed by the processor cause the system further cause the system to determine distances between occlusal surfaces of a first tooth of a first of the upper and lower arches and a second tooth of a second of the upper and lower arches in occlusion with the first tooth based on the fourth 3D model.

Clause 78. The non-transitory computer readable medium of clause 77, wherein the instructions that when executed by the processor further cause the system to generate an occlusion map on occlusal surfaces of the first tooth based on the determined distances.

Clause 79. The non-transitory computer readable medium of clause 69, wherein the instructions that when executed by the processor further cause the system to determine distances between occlusal surfaces of teeth of a first of the upper and lower arches and a teeth of a second of the upper and lower arches in occlusion with the teeth of the first of the arches based on the fourth 3D model.

Clause 80. The non-transitory computer readable medium of clause 79, wherein the instructions that when executed by the processor further cause the system to generate an occlusion map on occlusal surfaces of the teeth of the first arch based on the determined distances.

Clause 81. The non-transitory computer readable medium of clause 69, wherein the instructions that when executed by the processor further cause the system to generate a movement vector between a position and orientation of a tooth in one of the first or second 3D digital models and a position and orientation of the tooth in the fourth 3D digital model.

Clause 82. The non-transitory computer readable medium of clause 69, wherein the instructions that when executed by the processor cause the system to generate the third 3D digital model of the patient's upper and lower arches in biting occlusion further includes instructions that cause the system to generate a plurality of third 3D digital models of the patient's upper and lower arches in biting occlusion, each of the plurality of third digital models being generated based on data generated while the patient's arches are under a different one of a plurality of biting loads.

Clause 83. The non-transitory computer readable medium of clause 82, wherein the instructions that when executed by the processor cause the system to generate the third 3D digital model of the patient's upper and lower arches in biting occlusion align teeth of the first and second 3D digital models with corresponding teeth of the third 3D digital model to generate the fourth 3D model of the patient's teeth in biting occlusion includes instructions to align teeth of the first and second 3D digital models with corresponding teeth of each of the plurality of third 3D digital model to generate a plurality of fourth 3D digital models of the patient's teeth in biting occlusion.

Clause 84. The non-transitory computer readable medium of clause 83, wherein the instructions that when executed by the processor further cause the system to determine a trace of a contact between a first tooth of a first of the upper and lower arches and a second tooth of a second of the upper and lower arches based on contact locations between the first tooth and the second tooth in the plurality of fourth 3D digital models.

Clause 85. The non-transitory computer readable medium of clause 83, wherein the instructions that when executed by the processor further cause the system to display the plurality of fourth 3D models of the teeth.

Clause 86. The non-transitory computer readable medium of clause 83, wherein the instructions that when executed by the processor further cause the system to generate a sequence of contacts between a plurality of opposing pairs of teeth based on the plurality of fourth 3D digital models.

Clause 87. The non-transitory computer readable medium of clause 83, wherein the instructions that when executed by the processor further cause the system to generate a treatment plan to move the patient's teeth from a first arrangement towards a second arrangement based on tooth positions in biting occlusion.

Clause 88. The non-transitory computer readable medium of clause 83, wherein the instructions that when executed by the processor further cause the system to: generate a treatment plan to move the patient's teeth from a first arrangement towards a second arrangement; and modify the tooth positions of one or more teeth during one or more stages of the treatment plan based on the tooth movements in biting occlusion.

Clause 89. The non-transitory computer readable medium of clause 83, wherein the instructions that when executed by the processor further cause the system to: generate a treatment plan to move the patient's teeth from a first arrangement towards a second arrangement; and modify the tooth positions of one or more teeth during one or more stages of the treatment plan based on the positions of the teeth in biting occlusion.

Clause 90. The non-transitory computer readable medium of clause 83, wherein the instructions that when executed by the processor further cause the system to: generate a treatment plan to move the patient's teeth from a first arrangement towards a second arrangement based on tooth positions in biting occlusion, wherein the second arrangement includes positioning a first tooth relative to a second tooth to limit movement of the first or second tooth during biting occlusion to less than a threshold amount.

Clause 91. The non-transitory computer readable medium of clause 90, wherein the threshold is 1 mm, 0.5 mm, or 0.25 mm.

Clause 92. The non-transitory computer readable medium of clause 88, wherein the instructions that when executed by the processor cause the system to modify the tooth positions further cause the system to place a cusp of a tooth of a first arch between cusps of a second tooth of a second arch in occlusion.

Clause 93. The non-transitory computer readable medium of clause 88, wherein modifying the tooth positions includes placing a cusp of a tooth of a first arch within a groove of a second tooth a second arch in occlusion.

Clause 94. The non-transitory computer readable medium of clause 86, wherein the sequence of contacts between the plurality of opposing pairs of teeth represent the order in which each of the plurality of opposing pairs of teeth come into contact with each other as the patient occlusally bites.

Clause 95. The non-transitory computer readable medium of clause 69, wherein the instructions that when executed by the processor further cause the system to: scan the patient's teeth in biting occlusion with a CBCT scanner to generate CBCT scan data, align the position of the patient's teeth in the fourth 3D digital model with the patient's teeth in the CBCT scan data to determine a position of a root of a tooth; and determine a location for placing an implant based on the position of the root of the tooth.

Clause 96. The non-transitory computer readable medium of clause 81, wherein the instructions that when executed by the processor further cause the system to generate an orthodontic retainer that accommodates the tooth movement based on the movement vector.

Clause 97. The non-transitory computer readable medium of clause 78, wherein the instructions that when executed by the processor further cause the system to generate an occlusal surface position for a prosthetic tooth based on the occlusion map to avoid occlusal contact with a tooth that opposes the prosthetic tooth.

Clause 98. The non-transitory computer readable medium of clause 97, wherein the prosthetic tooth is one of a crown, partial, or implant.

Clause 99. The non-transitory computer readable medium of clause 69, wherein the instructions that when executed by the processor cause the system to generate a first 3D digital model of the patient's lower arch in non-occlusion further causes the system to generate a first 3D digital model of a portion of the patient's lower arch in non-occlusion, the instructions that when executed by the processor cause the system to generate a second 3D digital model of the patient's upper arch in non-occlusion further causes the system to generate a second 3D digital model of a portion of the patient's lower arch in non-occlusion, and the instructions that when executed by the processor cause the system to generate a third 3D digital model of the patient's upper and lower arches in biting occlusion further causes the system to generate a third 3D digital model of the portion of the patient's upper arch and the portion of the lower arch in biting occlusion.

Clause 100. The non-transitory computer readable medium of any one of clauses 69-99, wherein the instructions that when executed by the processor further cause the system generate instructions for fabricating an appliance based on the at least one of the 3D digital models.

Clause 101. The non-transitory computer readable medium of any one of clauses 69-99, wherein the instructions that when executed by the processor further cause the system fabricate an appliance based on the at least one of the 3D digital models.

Clause 102. The non-transitory computer readable medium of clause 101, wherein the appliance is an orthodontic aligner or a prosthetic tooth.

What is claimed is:

1. A method for determining biting occlusion of a patient's teeth:
   generating a first 3D digital model of the patient's lower arch in non-occlusion;
   generating a second 3D digital model of the patient's upper arch in non-occlusion;
   segmenting teeth in the first and second 3D digital models;
   generating a third 3D digital model of the patient's upper and lower arches in biting occlusion;
   prior to generating a treatment plan, aligning the segmented teeth of the first and second 3D digital models with positions of corresponding teeth of the third 3D digital model to generate a fourth 3D model of the patient's teeth in biting occlusion; and
   generating the treatment plan to move the patient's teeth towards a target arrangement.

2. The method of claim 1, wherein generating the first 3D digital model includes scanning the patient's lower arch, generating the second 3D digital model includes scanning the patient's upper arch, and generating the third 3D digital model includes scanning the patient's upper and lower arches in biting occlusion.

3. The method of claim 1, wherein the first 3D digital model includes data representing the buccal, occlusal, lingual, mesial, and distal surfaces of the teeth of the patient's lower arch and the second 3D digital model includes data representing the buccal, occlusal, lingual, mesial, and distal surfaces of the teeth of the patient's upper arch.

4. The method of claim 3, wherein the third 3D digital model includes data representing the buccal surfaces of the patient's upper and lower arches.

5. The method of claim 1, wherein generating the third 3D digital model of the patient's upper and lower arches in biting occlusion includes generating the third 3D digital model based on data generated when a biting force is applied to the patient's arches.

6. The method of claim 1, wherein generating the third 3D digital model of the patient's upper and lower arches in biting occlusion includes generating a plurality of third 3D digital models of the patient's upper and lower arches in biting occlusion, each of the plurality of third digital models being generated based on data generated while the patient's arches are under a different one of a plurality of biting loads.

7. The method of claim 6, wherein aligning teeth of the first and second 3D digital models with corresponding teeth of the third 3D digital model to generate the fourth 3D model of the patient's teeth in biting occlusion includes aligning teeth of the first and second 3D digital models with corresponding teeth of each of the plurality of third 3D digital model to generate a plurality of fourth 3D digital models of the patient's teeth in biting occlusion.

8. The method of claim 7, further comprising determining a trace of a contact between a first tooth of a first of the upper and lower arches and a second tooth of a second of the upper and lower arches based on contact locations between the first tooth and the second tooth in the plurality of fourth 3D digital models.

9. The method of claim 7, further comprising generating a sequence of contacts between a plurality of opposing pairs of teeth based on the plurality of fourth 3D digital models.

10. The method of claim 7, further comprising:
    generating a treatment plan to move the patient's teeth from a first arrangement towards a second arrangement based on tooth positions in biting occlusion.

11. The method of claim 7, further comprising:
    generating a treatment plan to move the patient's teeth from a first arrangement towards a second arrangement; and
    modifying the tooth positions of one or more teeth during one or more stages of the treatment plan based on the tooth movements in biting occlusion.

12. The method of claim 11, wherein modifying the tooth positions includes placing a cusp of a tooth of a first arch within a groove of a second tooth a second arch in occlusion.

13. The method of claim 7, further comprising:
    generating a treatment plan to move the patient's teeth from a first arrangement towards a second arrangement; and
    modifying the tooth positions of one or more teeth during one or more stages of the treatment plan based on the positions of the teeth in biting occlusion.

14. The method of claim 7, further comprising:
    generating a treatment plan to move the patient's teeth from a first arrangement towards a second arrangement based on tooth positions in biting occlusion, wherein the second arrangement includes positioning a first tooth relative to a second tooth to limit movement of the first or second tooth during biting occlusion to less than a threshold amount.

15. The method of claim 14, wherein the threshold is 1 mm, 0.5 mm, or 0.25 mm.

16. The method of claim 1, further comprising:
    scanning the patient's teeth in biting occlusion with a CBCT scanner to generate CBCT scan data,
    aligning the position of the patient's teeth in the fourth 3D digital model with the patient's teeth in the CBCT scan data to determine a position of a root of a tooth; and
    determining a location for placing an implant based on the position of the root of the tooth.

17. A system comprising:
    a processor; and
    memory having instructions that when executed by the processor, cause the system to:
    generate a first 3D digital model of the patient's lower arch in non-occlusion;
    generate a second 3D digital model of the patient's upper arch in non-occlusion;
    segment teeth in the first and second 3D digital models;
    generate a third 3D digital model of the patient's upper and lower arches in biting occlusion; and
    prior to generating a treatment plan, align the segmented teeth of the first and second 3D digital models with positions of corresponding teeth of the third 3D digital model to generate a fourth 3D model of the patient's teeth in biting occlusion; and
    generate a treatment plan to move the patient's teeth towards a target arrangement.

18. A non-transitory computer readable medium, having stored thereon, instructions that when executed by a computing device, cause the computing device to:
- generate a first 3D digital model of the patient's lower arch in non-occlusion;
- generate a second 3D digital model of the patient's upper arch in non-occlusion;
- segment teeth in the first and second 3D digital models;
- generate a third 3D digital model of the patient's upper and lower arches in biting occlusion; and
- prior to generating a treatment plan, align the segmented teeth of the first and second 3D digital models with positions of corresponding teeth of the third 3D digital model to generate a fourth 3D model of the patient's teeth in biting occlusion; and
- generate a treatment plan to move the patient's teeth towards a target arrangement.

* * * * *